US009127255B2

(12) United States Patent
Jensen

(10) Patent No.: US 9,127,255 B2
(45) Date of Patent: Sep. 8, 2015

(54) 3-DIMENSIONAL SCAFFOLDS FOR IMPROVED DIFFERENTIATION OF PLURIPOTENT STEM CELLS TO HEPATOCYTES

(75) Inventor: Janne Jensen, Gothenburg (SE)

(73) Assignee: Takara Bio Europe AB, Gothenburg (SE)

( * ) Notice: Subject to any disclaimer, the term of this patent is extended or adjusted under 35 U.S.C. 154(b) by 0 days.

(21) Appl. No.: 13/703,495

(22) PCT Filed: Jun. 14, 2011

(86) PCT No.: PCT/EP2011/059773

§ 371 (c)(1), (2), (4) Date: Feb. 6, 2013

(87) PCT Pub. No.: WO2011/154552

PCT Pub. Date: Dec. 15, 2011

(65) Prior Publication Data

US 2013/0164266 A1 Jun. 27, 2013
US 2013/0336933 A9 Dec. 19, 2013

Related U.S. Application Data

(60) Provisional application No. 61/353,678, filed on Jun. 11, 2010.

(30) Foreign Application Priority Data

Jun. 11, 2010 (DK) ................................ 2010 00515

(51) Int. Cl.
*A61F 2/04* (2013.01)
*C12N 5/071* (2010.01)

(52) U.S. Cl.
CPC .............. *C12N 5/0671* (2013.01); *C12N 5/067* (2013.01); *C12N 2501/999* (2013.01); *C12N 2506/02* (2013.01); *C12N 2533/50* (2013.01)

(58) Field of Classification Search
None
See application file for complete search history.

(56) References Cited

U.S. PATENT DOCUMENTS

2009/0123432 A1* 5/2009 Heins et al. .................. 424/93.7

FOREIGN PATENT DOCUMENTS

CN 1844373 10/2006
CN 101428154 5/2009

OTHER PUBLICATIONS

Aejaz et al. “Stem cell therapy-present status”, Transplantation Proceedings 39: 694-99, 2007.*

Lees et al. “Transplantation of 3D scaffolds seeded with human embryonic stem cells: biological features of surrogate tissue and teratoma-forming potential.” Regenerative Med. (2007); 2(3), pp. 289-300.*

Soto-Gutirrez et al. “Differentiation of mouse embryonic stem cells to hepatocyte-like cells by co-culture with human liver nonparenchymal cell lines.” Nature Protocols (2007); 2: pp. 347-356.*

Boldt, J. “Use of albumin: an update” British Journal of Anaesthesia (Jan. 2010) 104 (3): pp. 276-84.*

Watanabe et al. “A Rock inhibitor permits survival of dissociated human embryonic stem cells.” Nature Biotechnology (2007); 25(2): pp. 681-696.*

Si-Tayeb et al.“Highly Efficient Generation of Human Hepatocyte-Like Cells from Induced Pluripotent Stem Cells.” Hepatology (Jan. 2010);51(1): pp. 297-305.*

Glicklis et al. “Hepatocyte Behavior Within Three-Dimensional Porous Alginate Scaffolds.” Biotechnology and Bioengineering (2000);67(3): pp. 344-353.*

Bokhari et al. “Culture of HepG2 liver cells on three dimensional polystyrene scaffolds enhances cell structure and function during toxicological challenge.” J. Anat. (2007); 211: pp. 567-576.*

Hayman et al. “Enhanced neurite outgrowth by human neurons grown on solid three-dimensional scaffolds.” Biochemical and Biophysical Research Communications (2004); 314: pp. 483-488.*

Wen et al. “Development of poly (lactic-co-glycolic acid)-collagen scaffolds for tissue engineer.” Materials Science and Engineering C 27 (2007); pp. 285-292.*

H. Baharvand et al., *Differentiation of human embryonic stem cells into hepatocytes in 2D and 3D culture systems in vitro*, 50(7) Int. J. Dev. Biol. 645-652 (2006).

S. Kazemnejad et al., *Functional hepatocyte-like cells derived from human bone marrow mesenchymal stem cells on a novel 3-dimensional biocompatible nanofibrous scaffold*, 31(6) International Journal of Artificial Organs 500-507 (Jun. 2008).

J. Lees et al., *Transplantation of 3D scaffolds seeded with human embryonic stem cells: biological features of surrogate tissue and teratoma-forming potential*, 2(3) Regenerative Medicine 289-300 (May 2007).

(Continued)

*Primary Examiner* — Thaian N Ton
*Assistant Examiner* — Titilayo Moloye
(74) *Attorney, Agent, or Firm* — Buchanan Ingersoll & Rooney PC

(57) ABSTRACT

The present invention relates to the use of 3-dimensional (3D) synthetic or animal-derived bioscaffolds as substrates for the improved growth and differentiation of hPS (Human pluripotent stem cells); these scaffolds being adapted for use in conjunction with existing cell culture lab plastic-ware. More specifically, it relates to the seeding of these scaffolds, either alone or in conjunction with various biologic matrix coatings, with hPS cells for the improved differentiation of said hPS cells into hepatocyte or hepatocyte-like cell types. The invention also relates to the seeding of partially-differentiated hepatocyte progenitors onto scaffolds for further differentiation into more mature hepatocyte-cell types.

26 Claims, 38 Drawing Sheets

(56) References Cited

OTHER PUBLICATIONS

Y. Sakai et al., *Toward engineering of vascularized three-dimensional liver tissue equivalents possessing a clinically significant mass*, 48(3) Biochemical Engineering Journal 348-361 (2010).

B. Tai et al., *The use of polyelectrolyte fibrous scaffold to deliver differentiated hMSCs to the liver*, 31(1) Biomaterials 48-57 (2010).

W. Turner et al., *Human Hepatoblast Phenotype Maintained by Hyaluronan Hydrogels*, 82B(1) Journal of Biomedical Materials Research 156-168 (Jul. 2007).

Chinese Office Action issued Dec. 18, 2013, in corresponding Chinese Application No. 201180037237.1 with English translation.

* cited by examiner

A

B

Figure 1 contd.
C
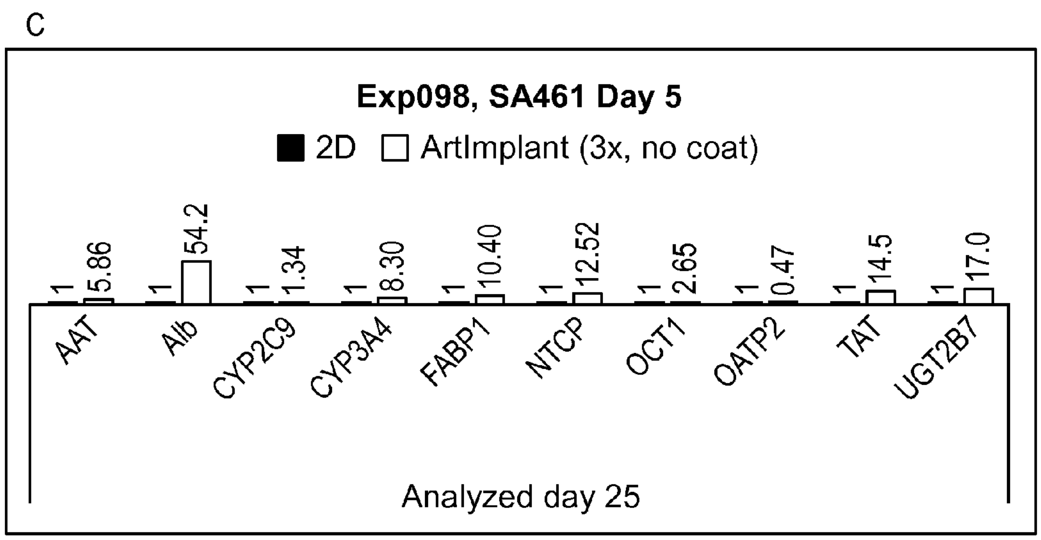
D
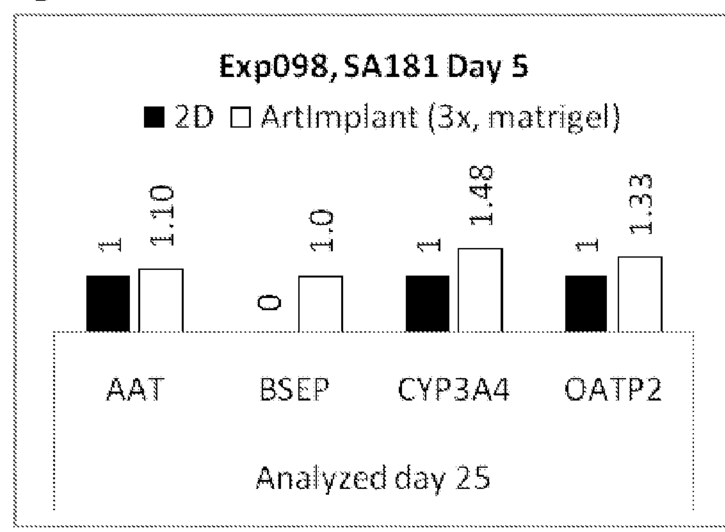

Figure 1 contd.
E
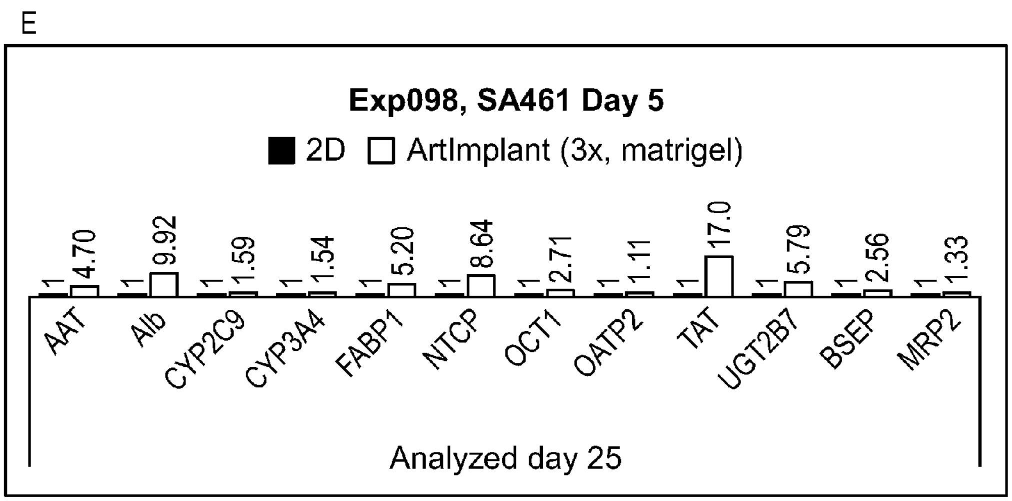
F
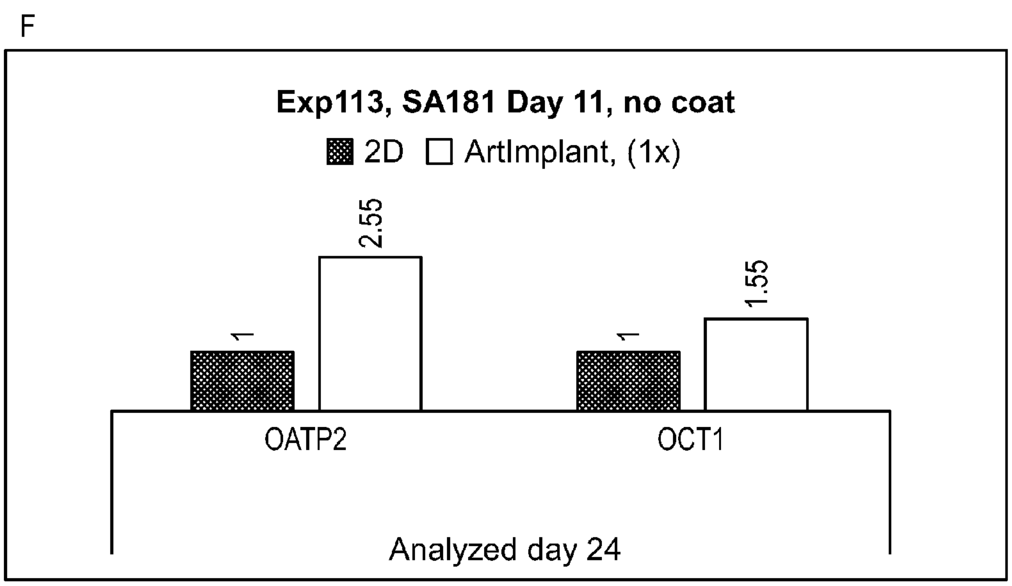

Figure 1 contd.
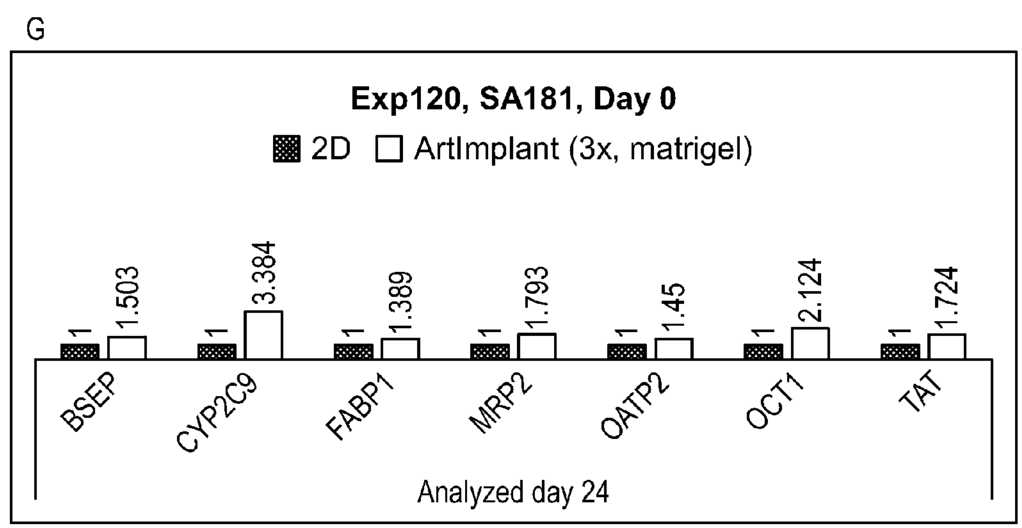

Figure 1 contd.
H
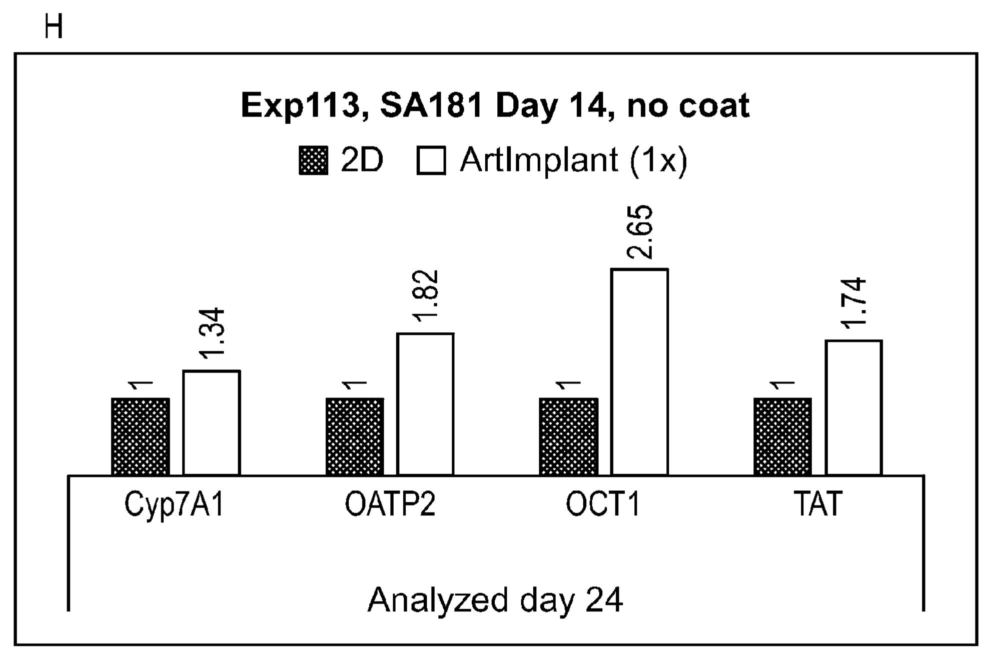
I
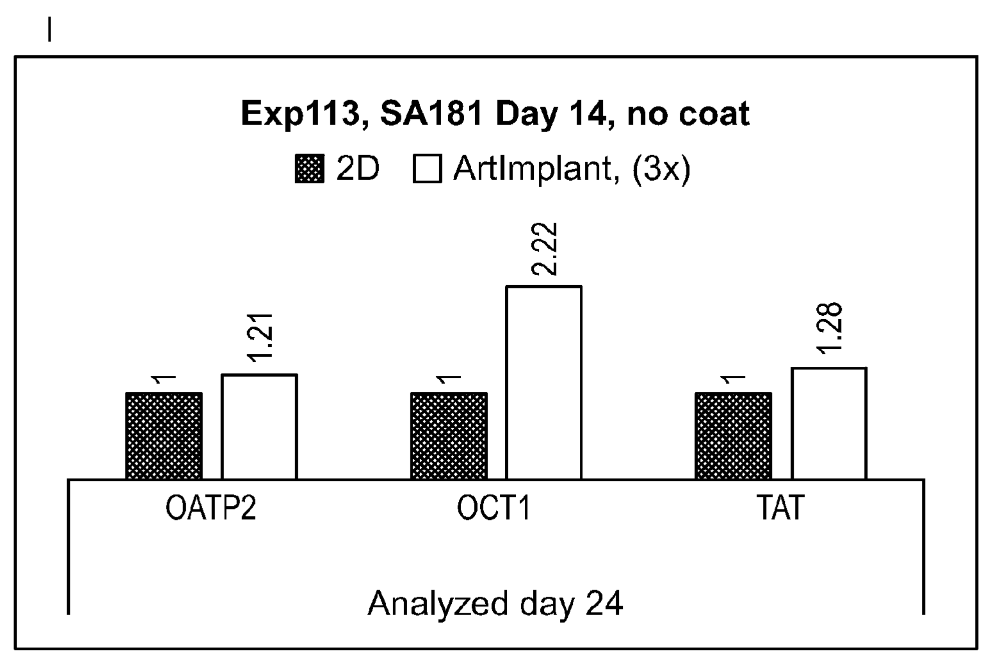

A

B

A

B

Figure 3 contd.
C
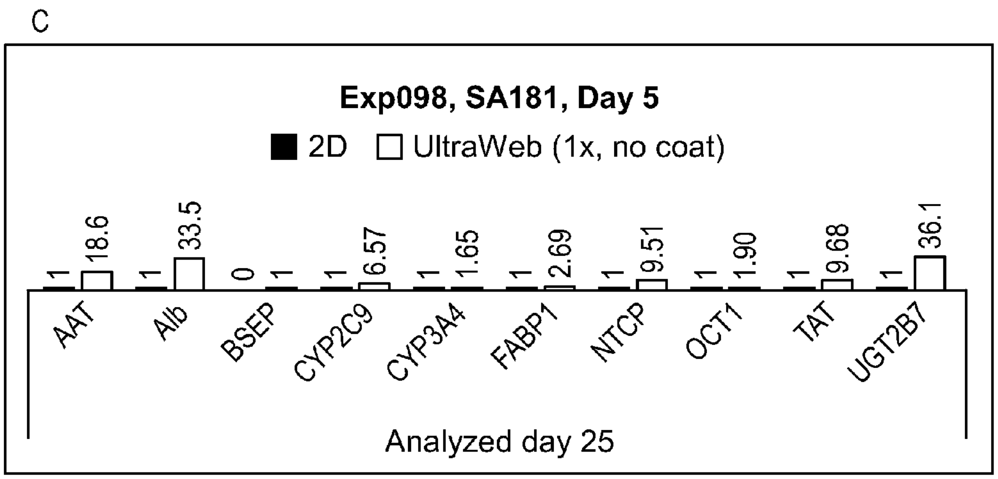
D
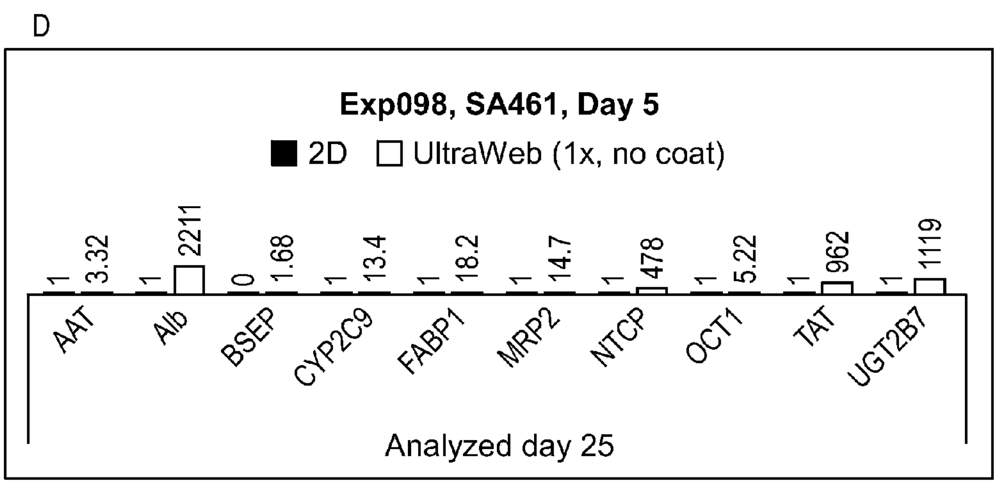

Figure 3 contd.
E
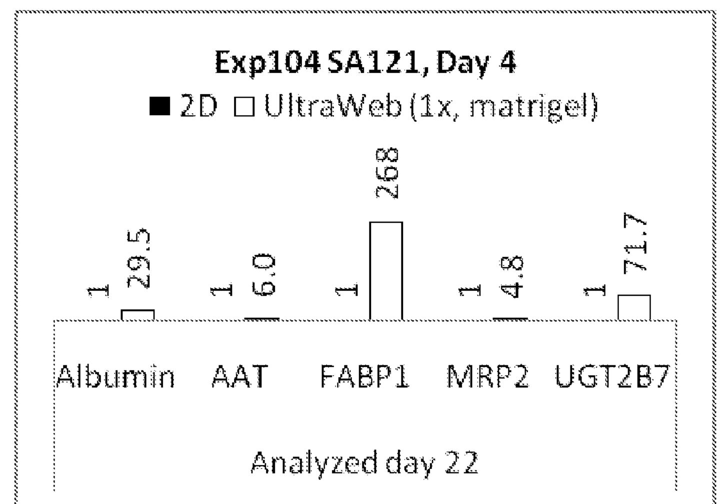
F
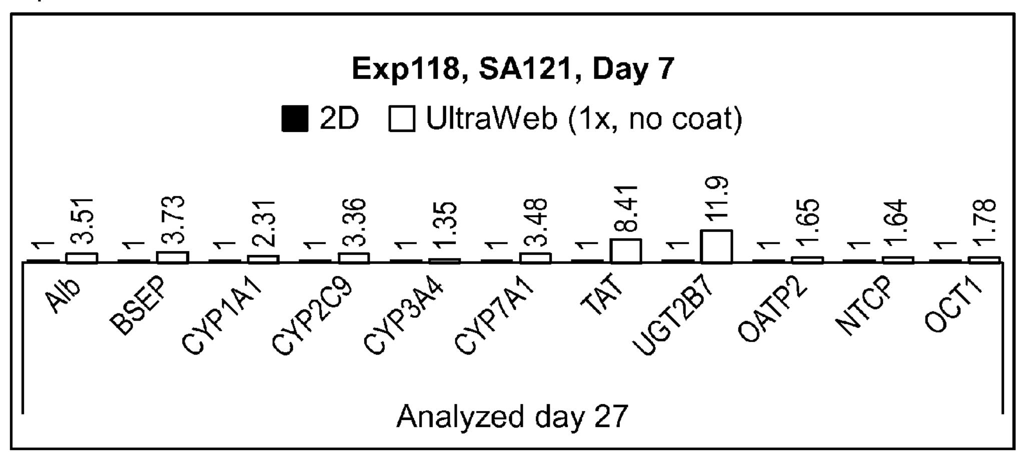

Figure 3 contd.
G
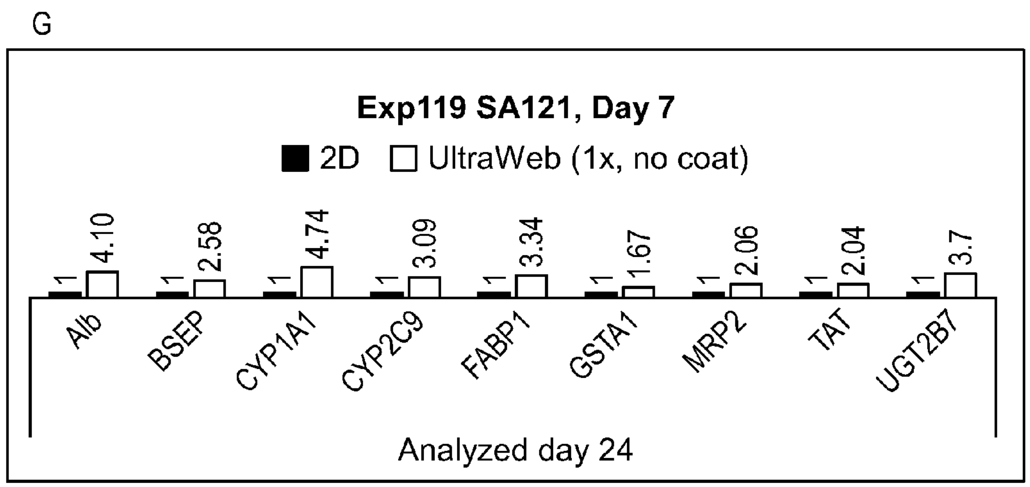
H
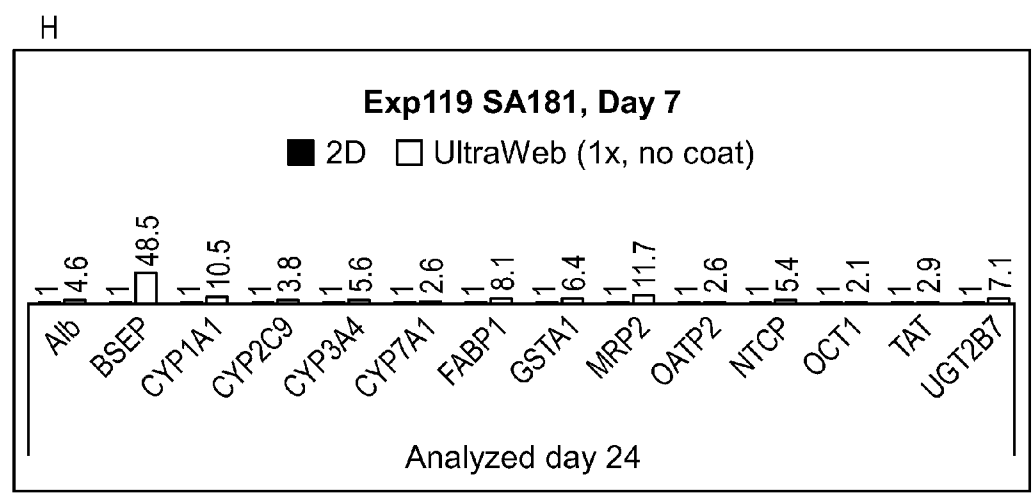

Figure 4a contd.
C
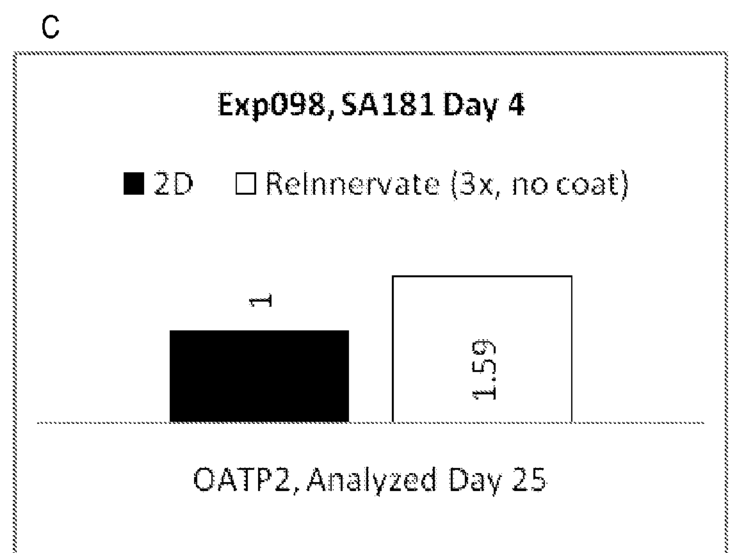
D
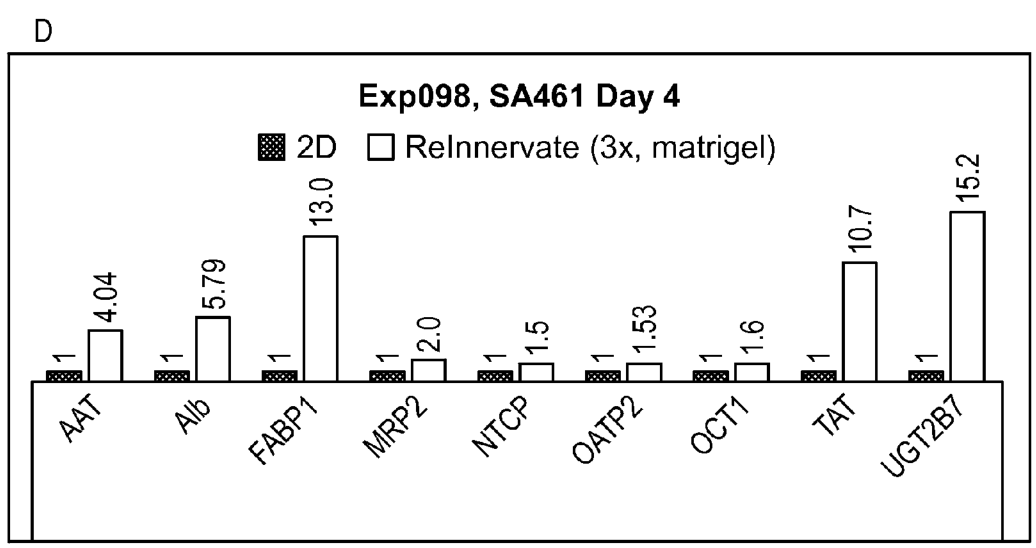

Figure 4a contd.
E
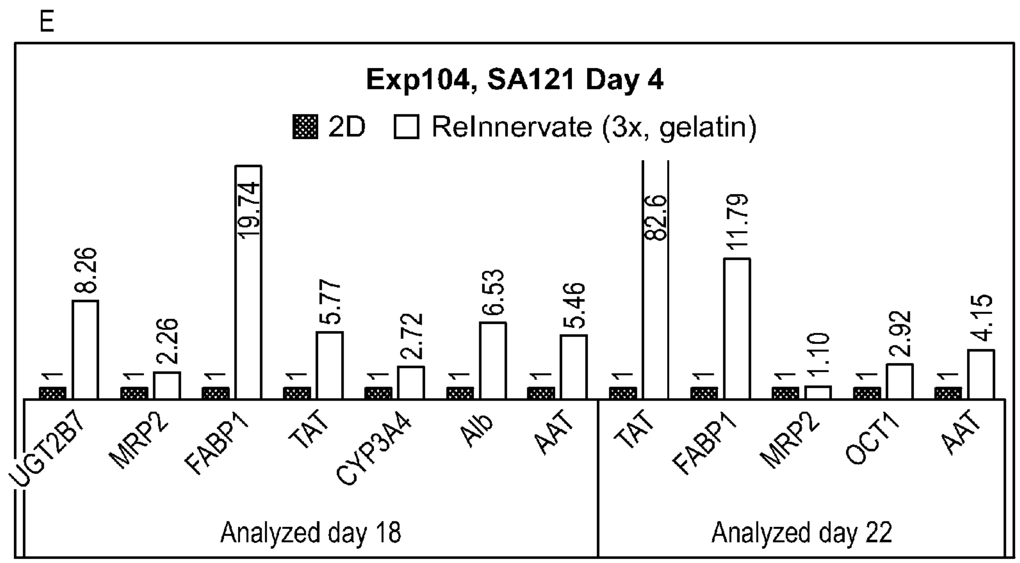
F
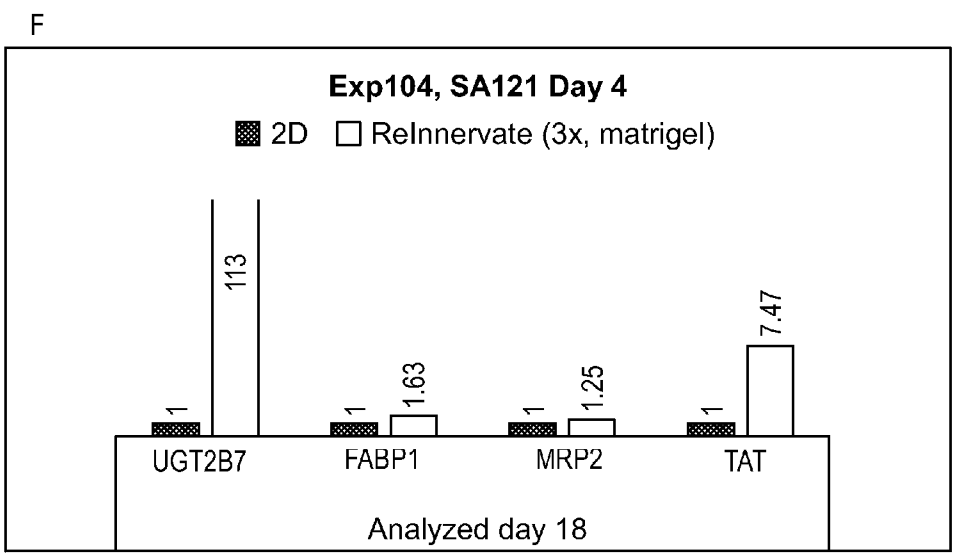

Figure 4a contd.
G
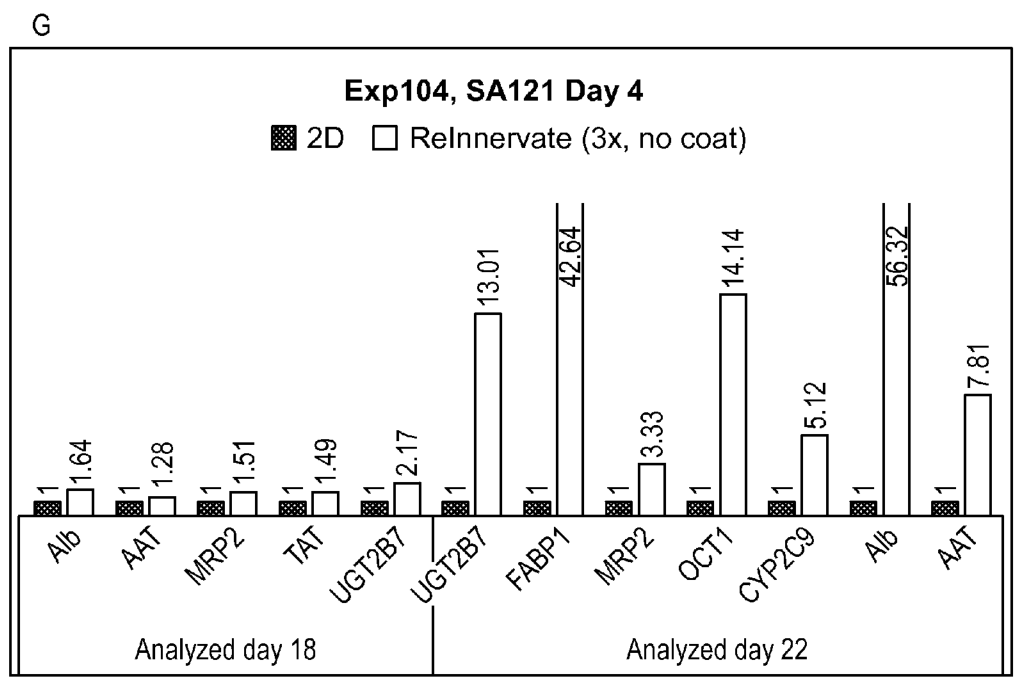
H
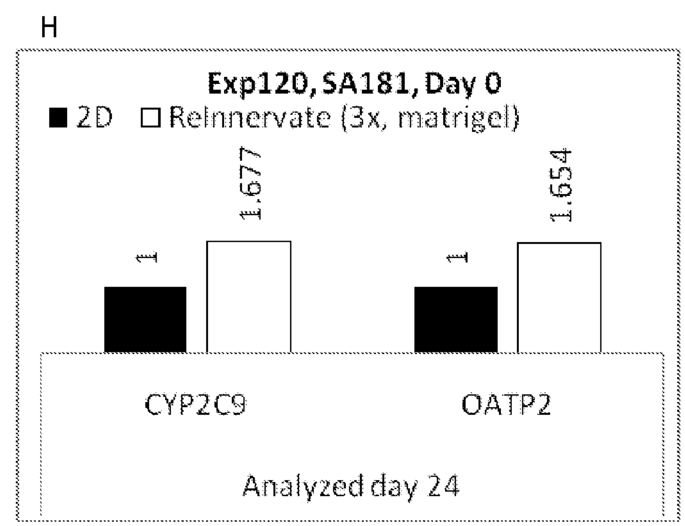

Figure 4a contd.
I
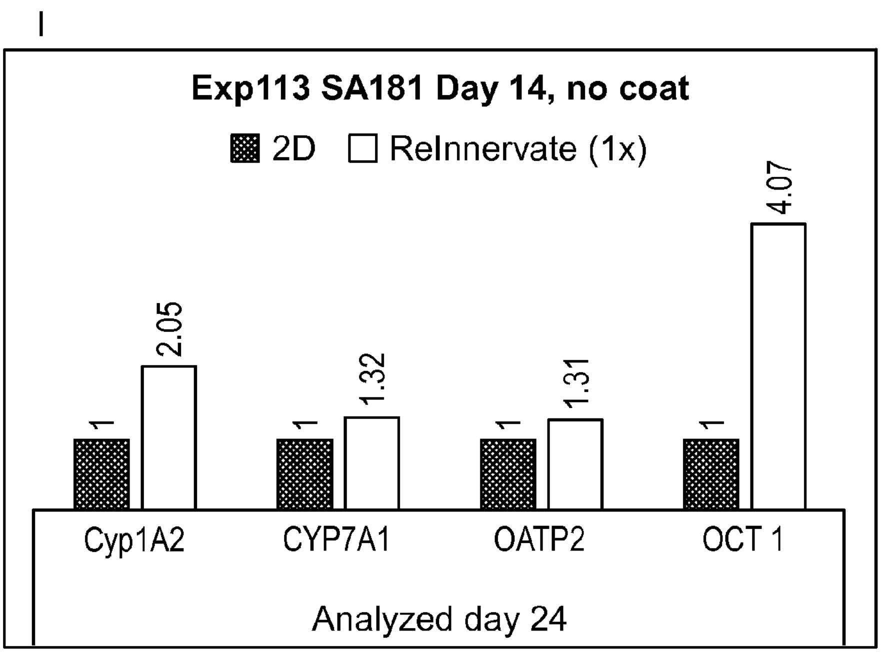
J
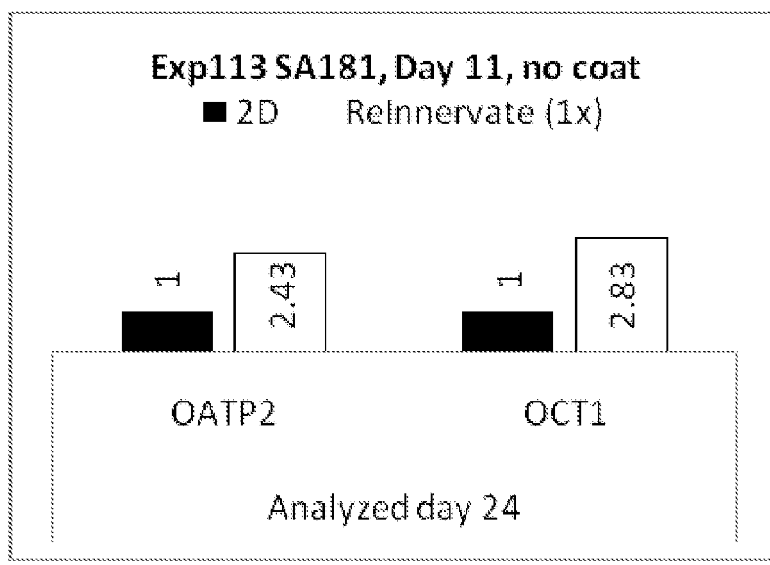

Figure 4a contd.
K
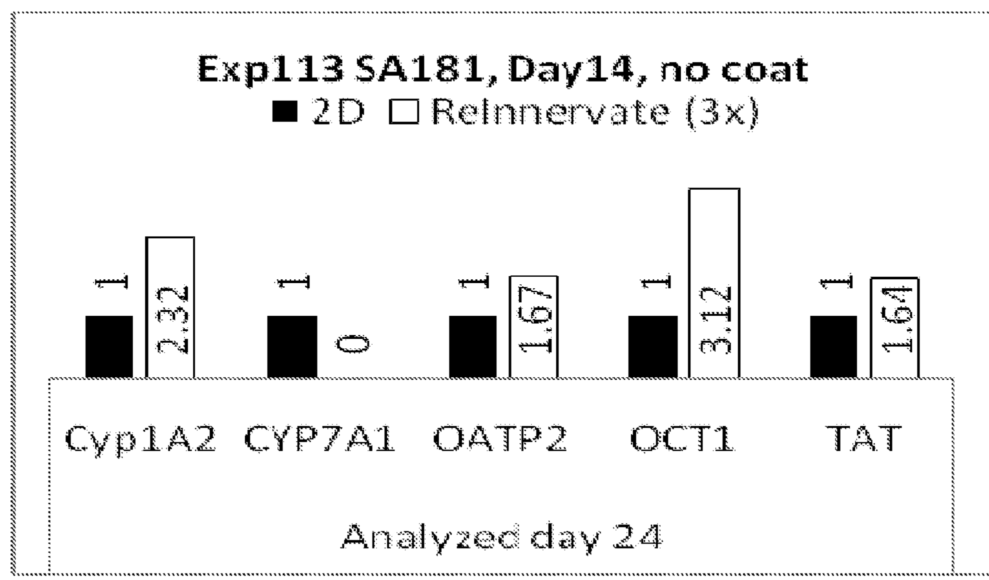
L
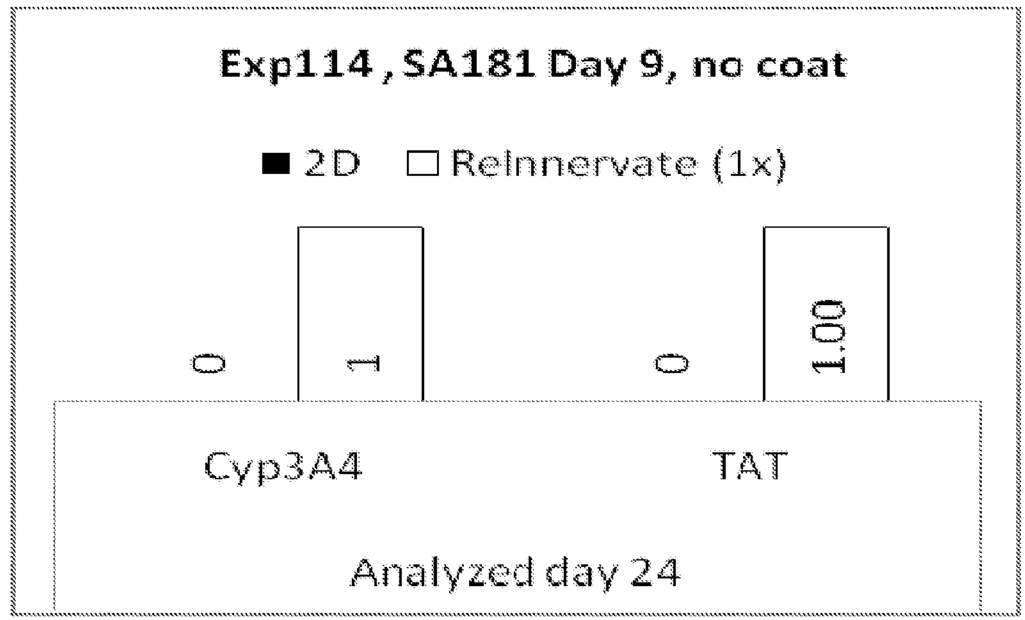

Figure 4a contd.
M
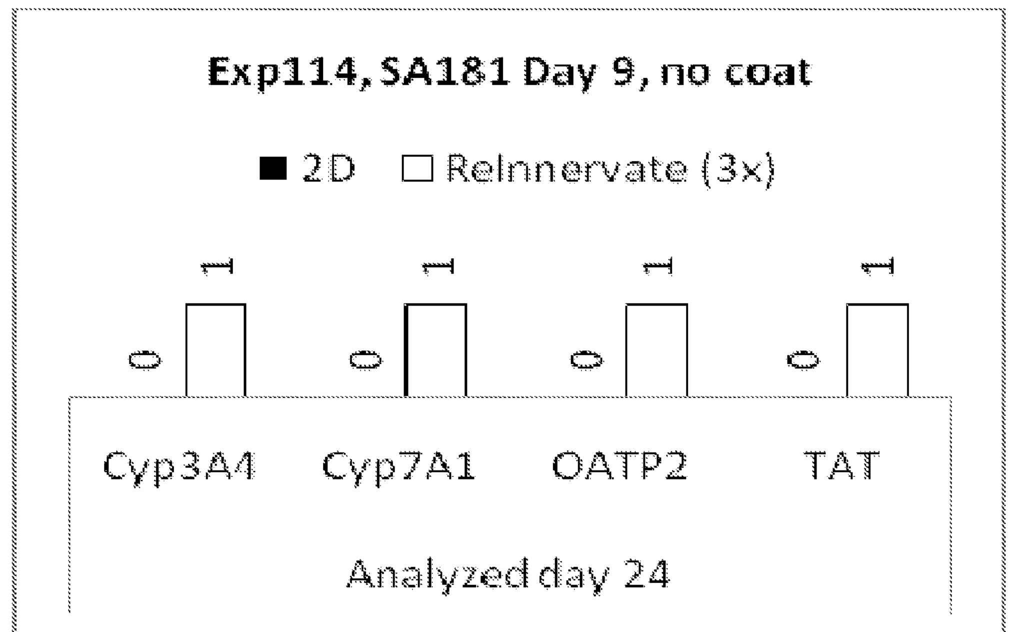
N
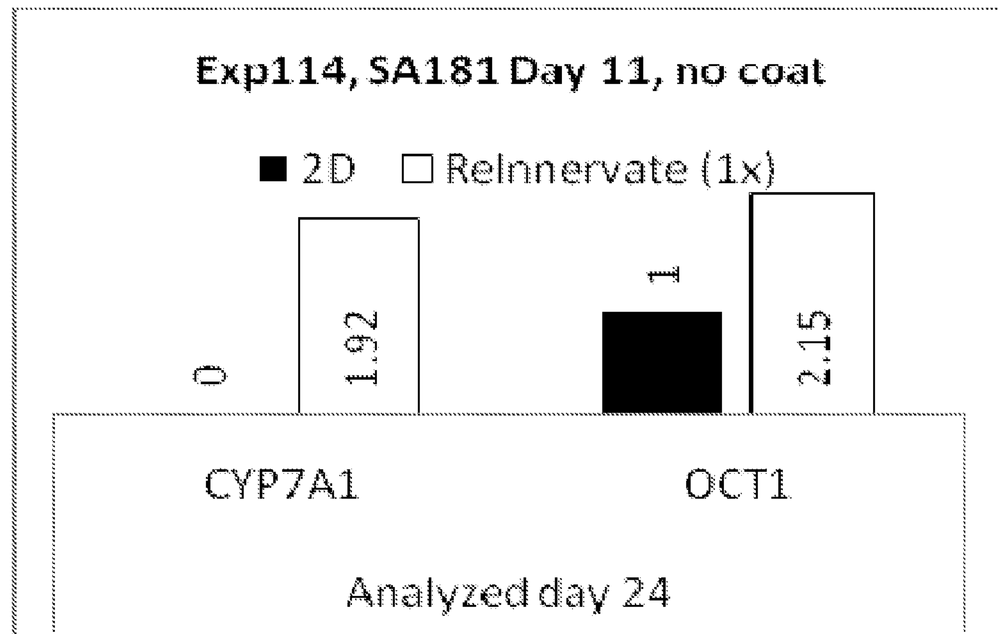

Figure 4a contd.
O
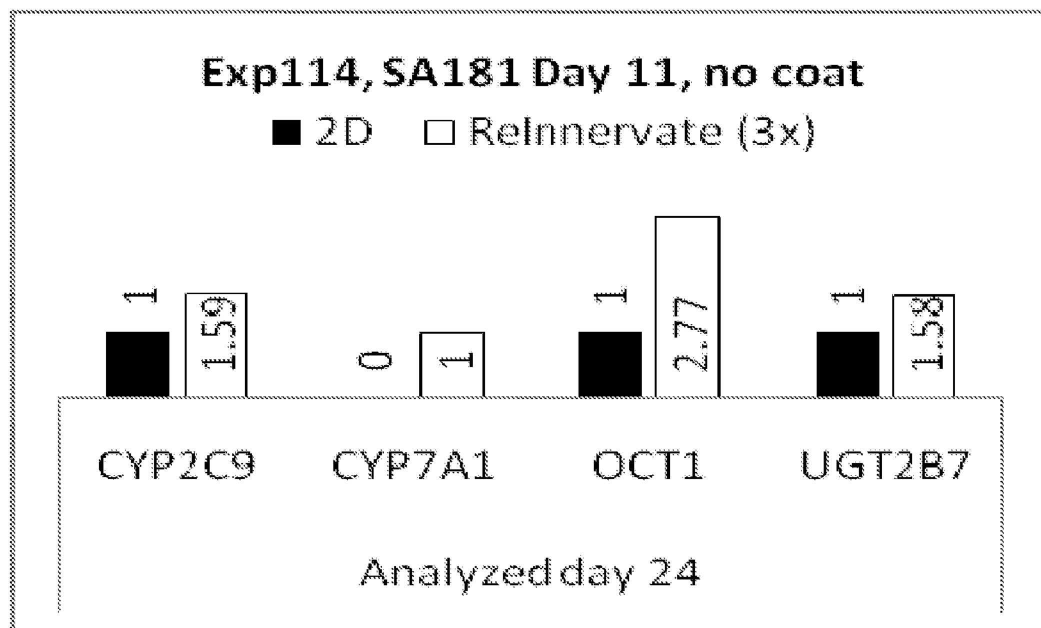
P
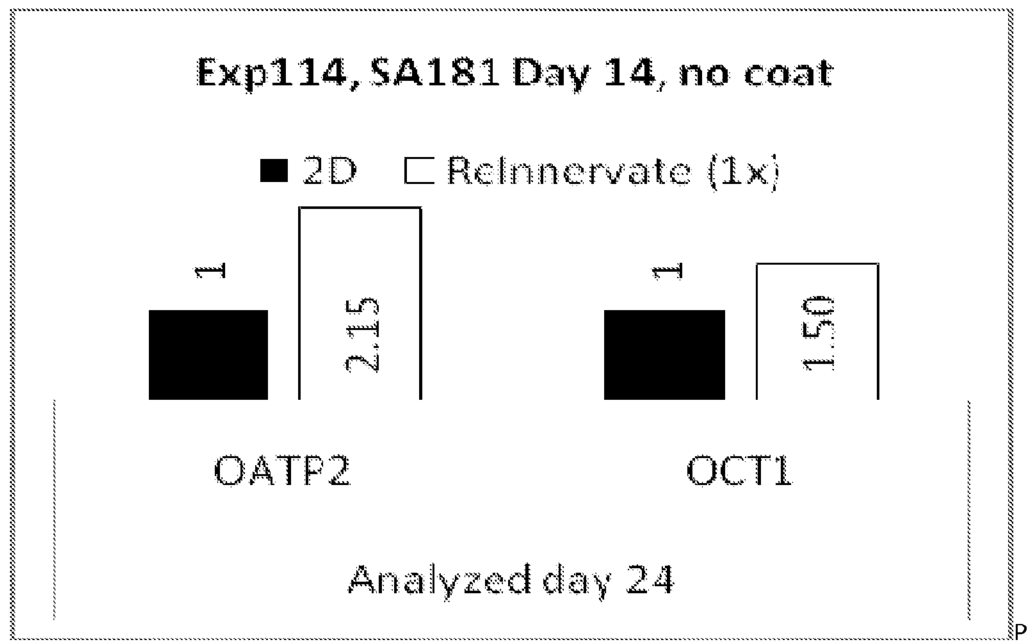

Figure 4a contd.
Q
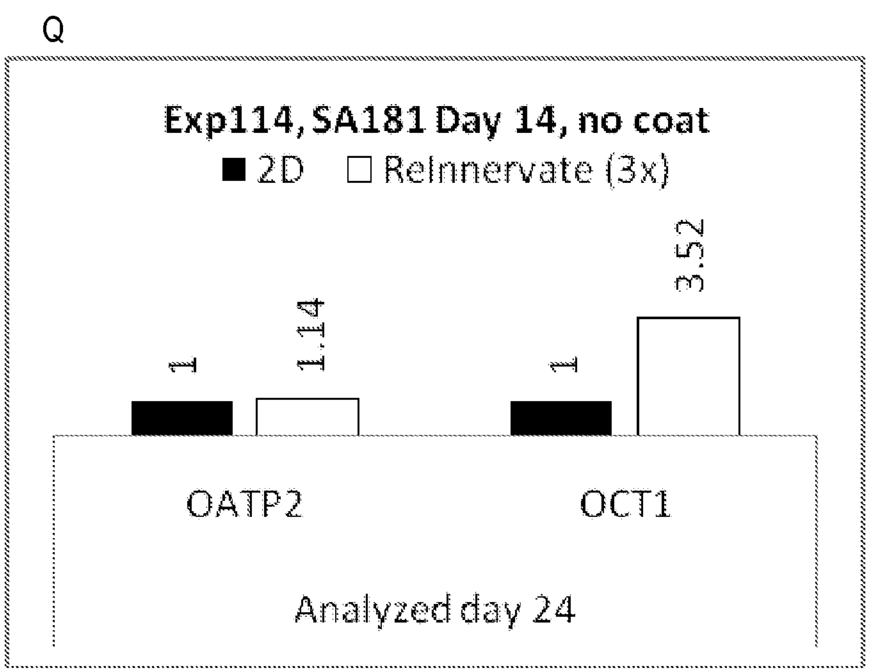
R
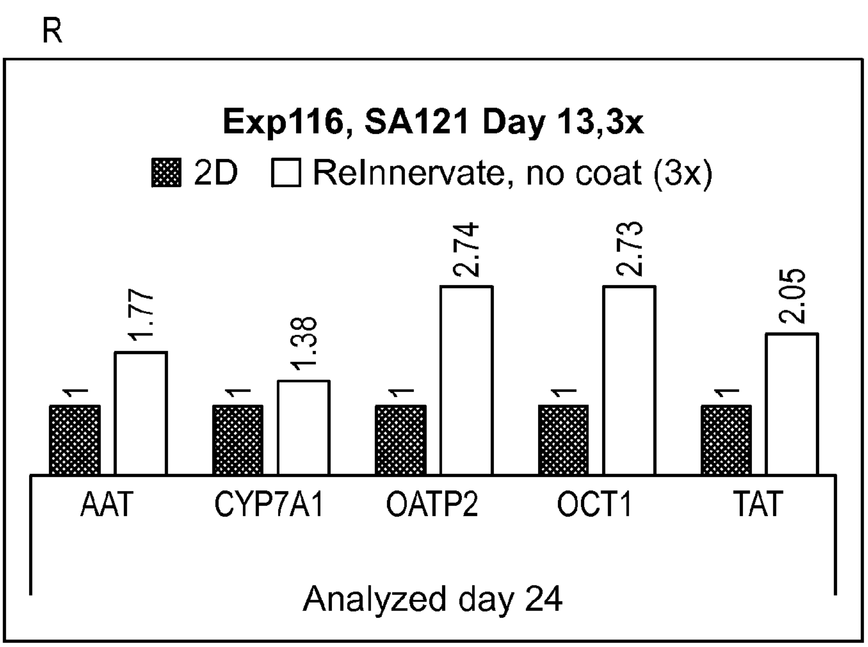

Figure 4a contd.
S
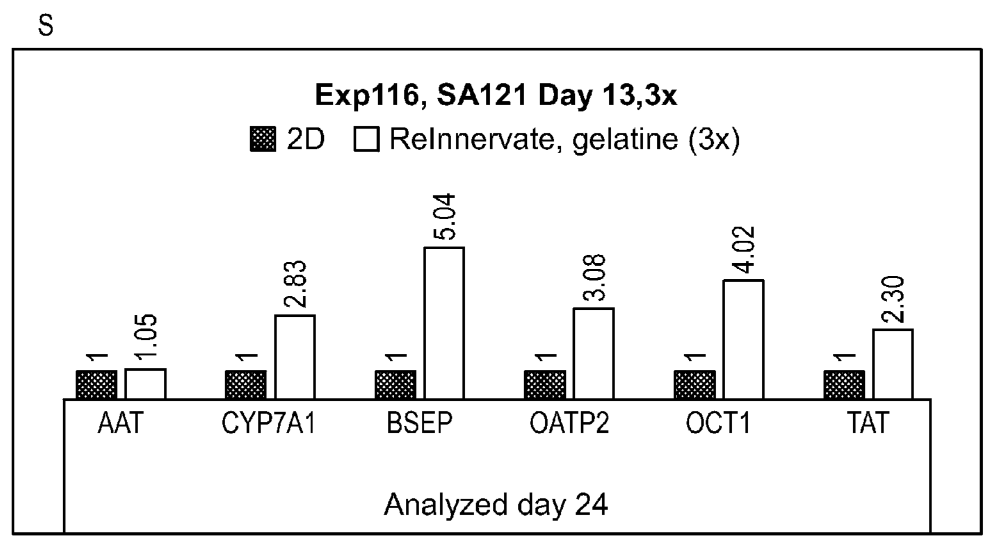

A

B

Figure 4b contd.
C
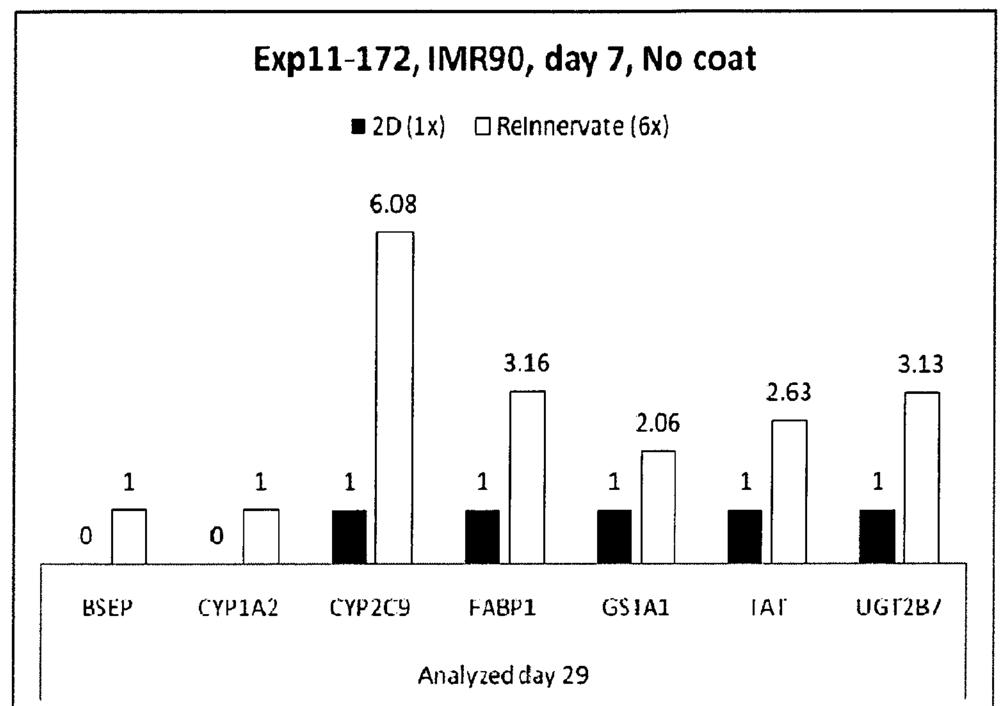

A

B

Figure 5a contd.
C
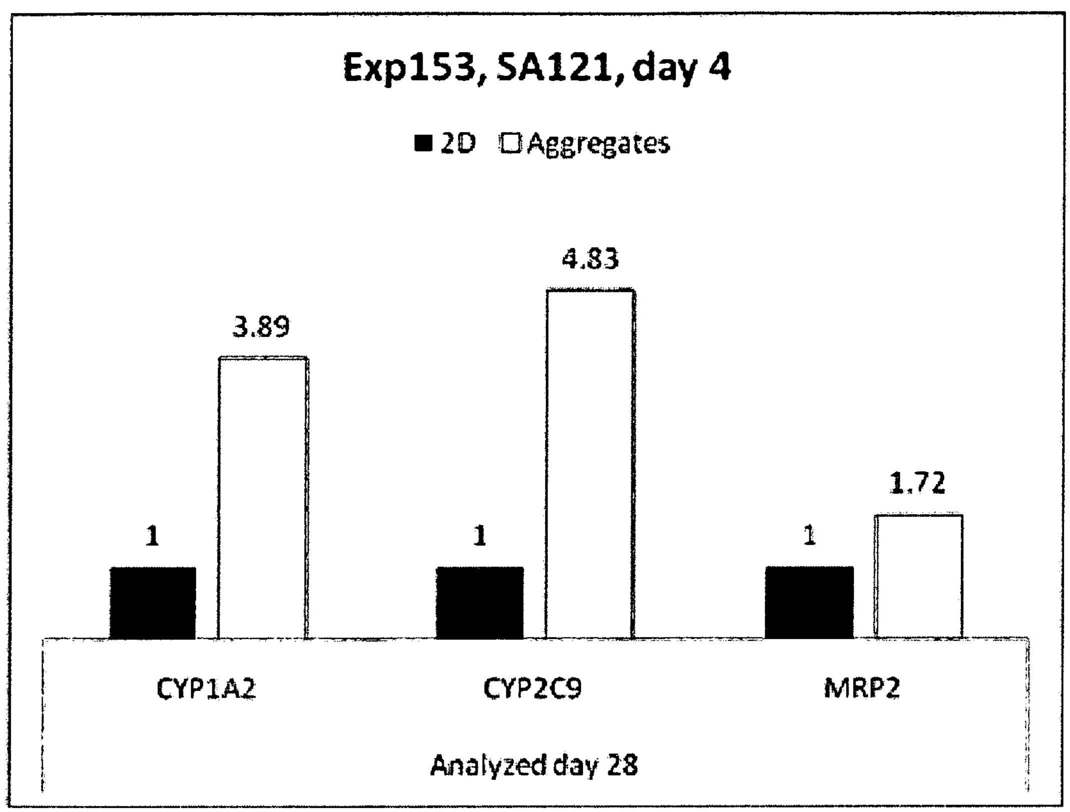

A

B

Figure 5b contd.
C
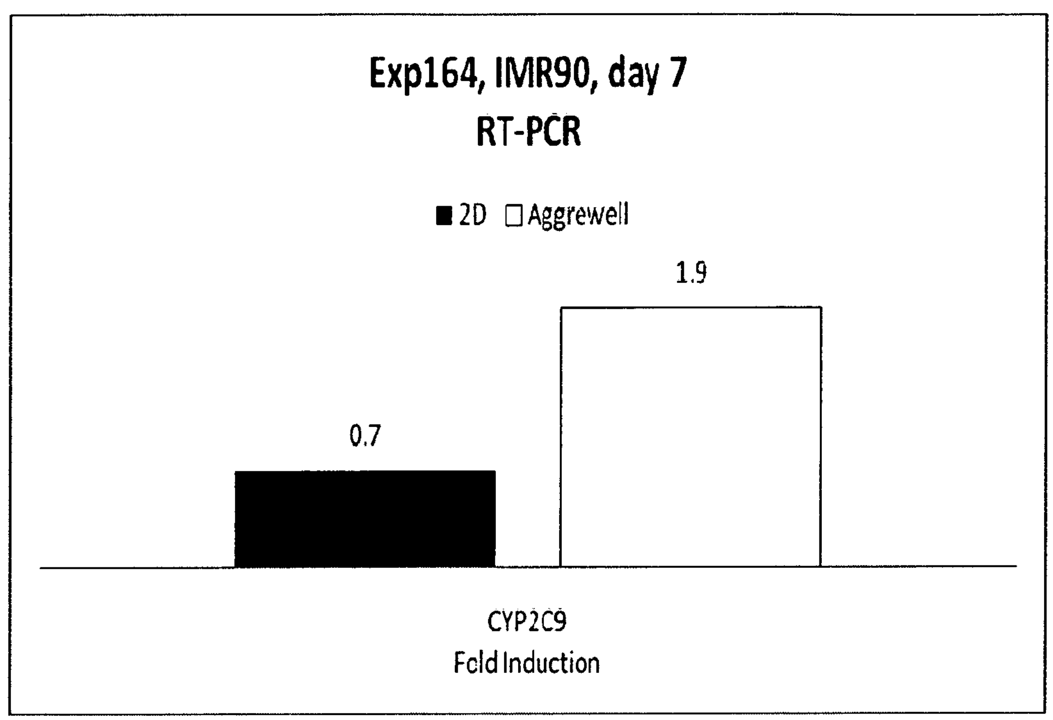

A

| | 2D (Day 23) | ReInnervate (Day 23) | 2D (Day 29) | ReInnervate (Day 29) |
|---|---|---|---|---|
| non ind | 1.63 | 10.53 | 0.99 | 6.63 |
| induced | 1.91 | 11.41 | 1.14 | 10.11 |

Figure 8 contd.
B
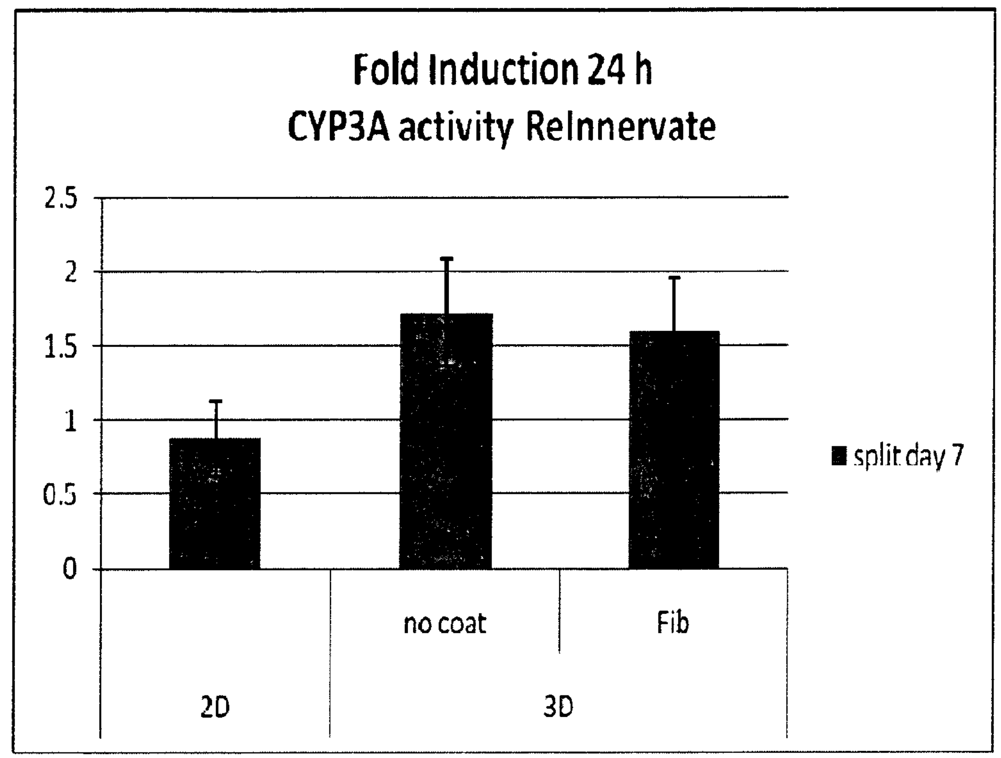
C
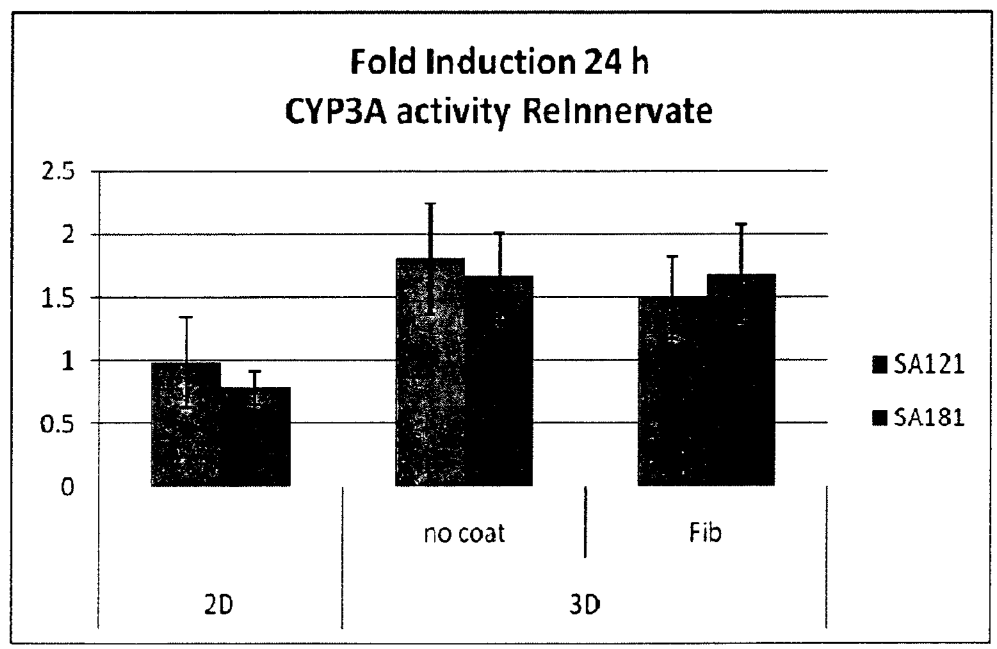

Figure 9 contd.
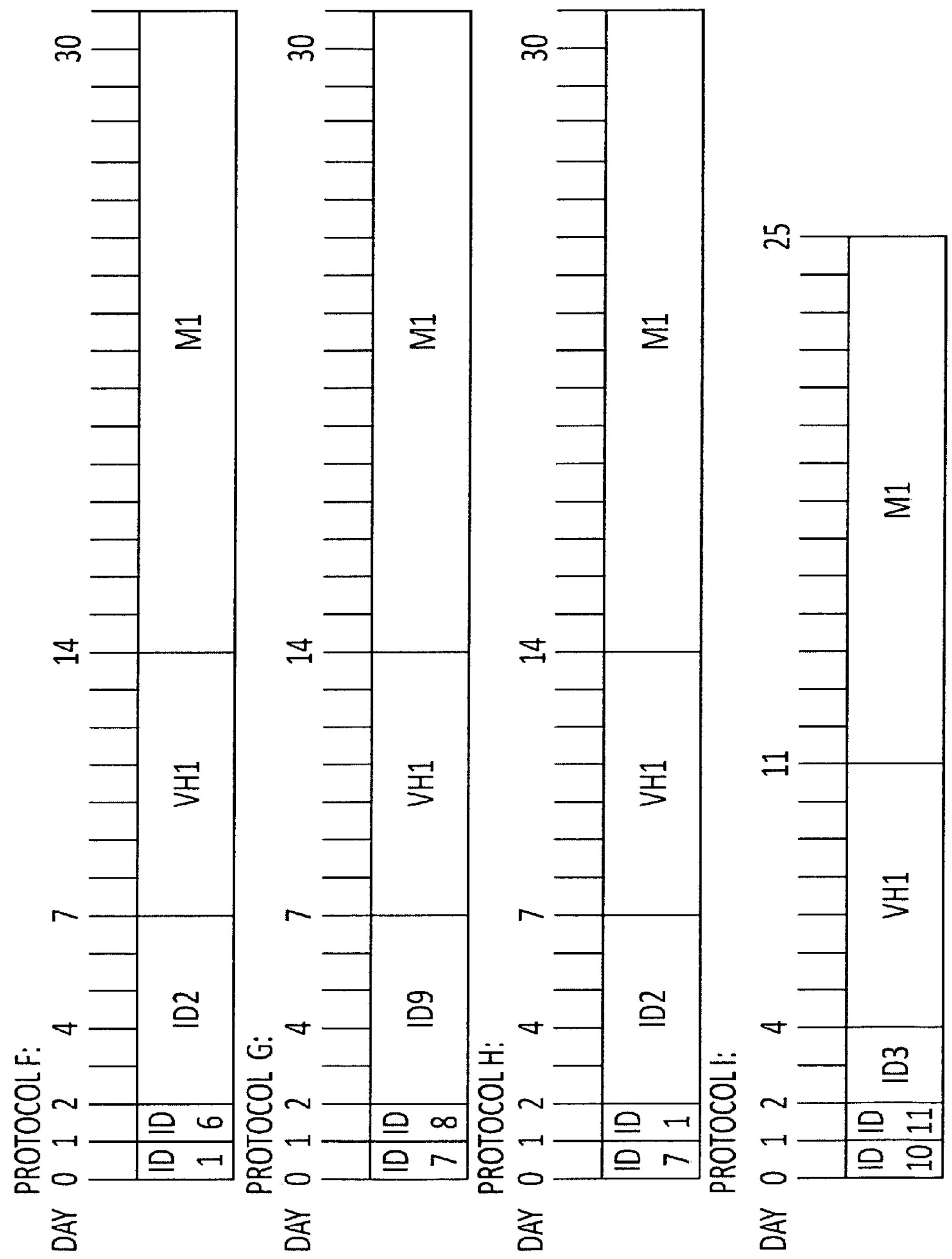

A

B

Figure 10 contd.
C
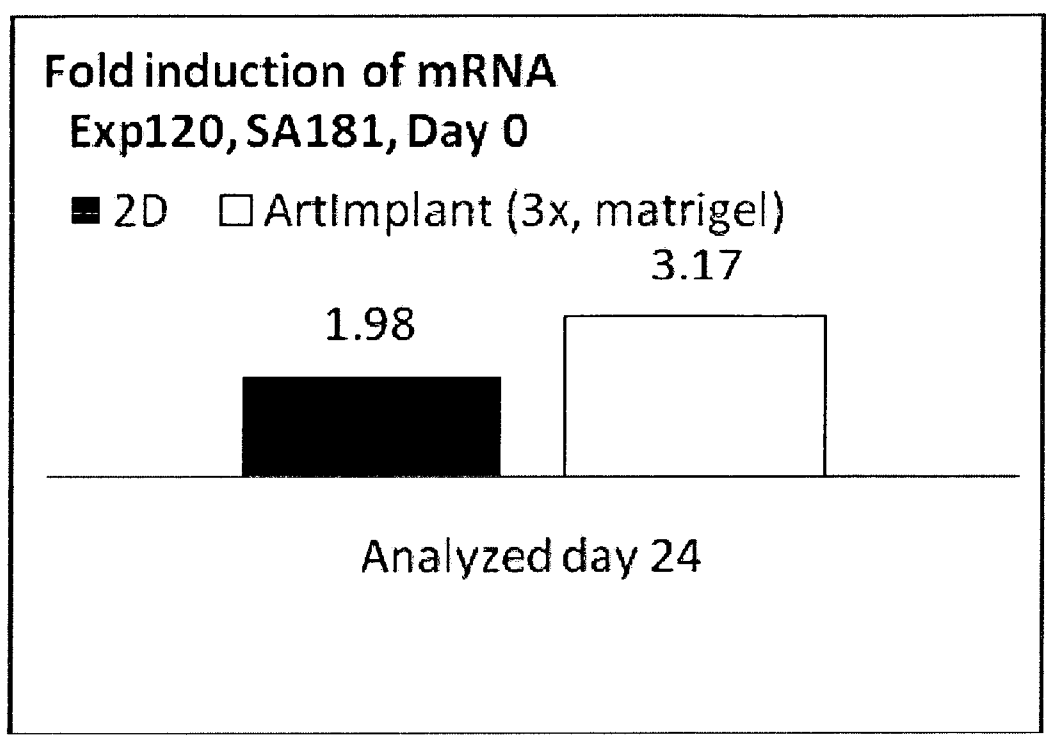

A

B

Figure 11a contd.
C
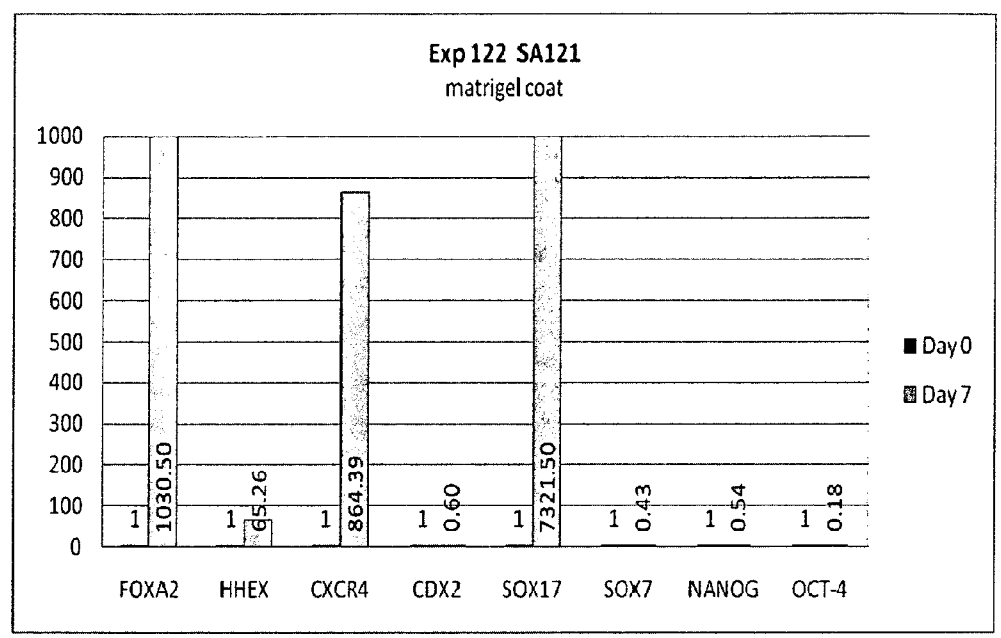
D
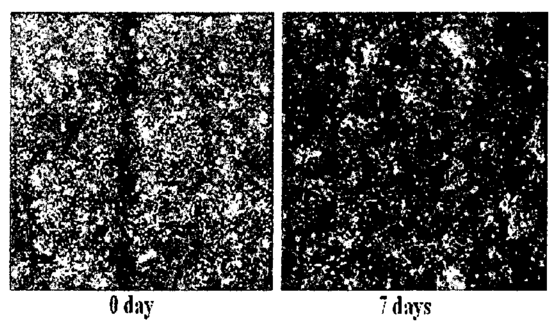
- Morphological changes are associated with a gene expression pattern specific for embryonic endoderm.

A

B

A

B

3-DIMENSIONAL SCAFFOLDS FOR IMPROVED DIFFERENTIATION OF PLURIPOTENT STEM CELLS TO HEPATOCYTES

CROSS-REFERENCE TO RELATED APPLICATIONS

This application is a U.S. National Stage patent application pursuant to 35 U.S.C. §371 of International Patent Application PCT/EP2011/059773, filed on Jun. 14, 2011, and published as WO 2011/154552 on Dec. 15, 2011, which claims priority to U.S. Provisional Patent Application Ser. No. 61/353,678, filed on Jun. 11, 2010, and Danish Patent Application PA 2010 00515, filed on Jun. 11, 2010, all of which are incorporated herein by reference in their entireties for all purposes.

TECHNICAL FIELD

The present invention relates to the use of 3-dimensional (3D) synthetic or animal-derived bioscaffolds as substrates for the improved growth and differentiation of hPS (Human pluripotent stem cells); these scaffolds being adapted for use in conjunction with existing cell culture lab plastic-ware. More specifically, it relates to the seeding of these scaffolds, either alone or in conjunction with various biologic matrix coatings, with hPS cells for the improved differentiation of said hPS cells into hepatocyte or hepatocyte-like cell types. The invention also relates to the seeding of partially-differentiated hepatocyte progenitors onto scaffolds for further differentiation into more mature hepatocyte-cell types.

BACKGROUND OF THE INVENTION

Mammalian Cell Culture

The process of mammalian cell culture has been refined and standardised over many years and the conditions required to permit cell growth, expansion and differentiation are well established. Cells can be routinely cultured on sterile plastic surfaces, such as polystyrene, often in conjunction with a matrix coating designed to more closely replicate the in vivo environment in which the cell would normally grow. In the case of embryonic stem cells, a layer of feeder cells such as mouse embryonic fibroblasts is often required to provide a better substrate to nourish and support the proliferation of the cells. Typically, mammalian cells will be cultured in a supportive medium usually containing additives such as foetal calf serum, which in addition to providing various hormones and growth factors to the cells also contains a number of cellular matrix components which again helps to replicate the ideal microenvironment for cell growth.

Currently, mammalian cell culture has a variety of downstream applications including their use in basic research, their use in drug and toxicology assays and their use in producing correctly folded recombinant mammalian proteins. More recently mammalian cell culture has been further developed to be used in the area of regenerative medicine, whereby tissue, such as skin dermal layers, is harvested and propagated for a certain time period in order to generate larger amounts of tissue for use in clinical surgery, e.g. repair of wounds after traumatic injury or repair of diseased internal organs. However, cells derived from primary sources are often very limited in their capacity to be further propagated and require complex formulations of growth medium and growth conditions to be successfully cultured. They also have limited use in regenerative medicine due to the problem of immune rejection.

Recently, there have been a number of developments in the field of embryonic stem cell research which aim to traverse these barriers. Not only can such pluripotent stem cells be propagated almost indefinitely, they also have the capacity to differentiate into every cell and tissue type which comprise the fully developed organism. As such, pluripotent stem cells can be an important tool in developing new drug assays and since their supply is virtually unlimited they provide a cheaper and less variable source.

3D Bioscaffolds

One of the main challenges in differentiating pluripotent stem cells has been to control differentiation in such a way as to consistently produce mature, fully functional cell types rather than partly differentiated, immature precursor cells or highly heterogeneous mixtures of various cell types. The simplest way to differentiate pluripotent stem cells is on a 2D plastic substrate but unfortunately this often produces differentiated cells which lack the characteristic phenotype of mature cell types. This is in part due to a failure to replicate the conditions experienced by stem cells during normal embryogenesis, a process which differs from 2D culture in that it does of course take place in 3 dimensions. One of the ways researchers have attempted to address this has been to develop novel 3D culture systems which aim to more faithfully replicate some of the conditions experienced by cells during embryogenesis and allow them to differentiate in a more natural way. In particular, such 3D systems allow cells to interact with each other to a greater degree and allow the development of complex multicellular aggregates more akin to functioning organs than anything that can be observed using 2D cell culture.

3D systems rely on the presence of a bioactive scaffold onto which the cells can be seeded and to which they can adhere. Such a scaffold must help to direct the growth and proliferation of cells in a desired 3D configuration and may also be required to provide certain molecular signals which help the cells to form the desired structures. Another important requirement of bioscaffolds is that they are scalable, so that tissue growth and cell differentiation can be carried out on a larger, more economical scale. Scaffolds may be composed of a variety of materials and correct scaffold selection may be crucial in directing the growth, proliferation and differentiation of any cells which are seeded onto it. For example, scaffolds are commonly composed of polymeric materials which are arranged into the form of a porous sponge. Cells seeded into this scaffold can then attach and grow inside the pore structure of the scaffold through the network of interconnecting tunnels and channels inside the scaffold, with pore size being an important consideration when selecting an appropriate scaffold. Bioactive agents, such as extracellular matrix (ECM) components, may also be used to enhance scaffold function when deposited onto a scaffold surface, permitting greater cell adhesion. The end result is to provide cells with an in vitro environment in which they can interact more realistically and in a manner which more closely resembles their normal in vivo home.

In several culture systems, the addition of extracellular matrix induces cellular polarity and tissue organisation. For example, when a monolayer of primary hepatocytes cultured on a flat sheet of collagen is further overlaid with a second layer of collagen, a so called sandwich culture, the cells show improved morphology and functionality compared to hepatocytes in conventional 2D cultures (Dunn, J. et al., 1991). The overlay causes the cells to maintain actin filaments similar to the in vivo state in contrast to the abnormal formation of stress fibres seen in the 2D control culture (Berthiaume, F. et al., 1996). The more physiological relevant cytoskeletal organisation and the following cell polarity and shape might be responsible for the improved hepatic functionality, although it was later argued that the beneficial effects of the sandwich culture primarily arise from the improved cell-cell contact rather than the cell contact to the extracellular matrix (Hamilton, G. et al., 2001). Collagen scaffolds has also been employed in the differentiation of embryonic stem cells into hepatocytes. Baharvand and co-workers found that differentiation of hepatocyte-like cells inside collagen scaffolds improved morphological features, gene expression pattern and metabolic activity compared to cells differentiated in traditional 2D (Baharvand, H. et al., 2006).

Alginate, which provides a porous non-adhesive 3D-scaffold support aggregation of hepatocytes to form strong cell-cell interaction leading to improved hepatic function (Dvir-Ginzberg, M. et al., 2003). The environment in the alginate matrix also supported differentiation of newborn rat hepatocytes (Dvir-Ginzberg, M. et al., 2008) and maturation of HepG2 (Elkayam, T. et al., 2006) into more mature, functional phenotypes. Additionally, the C3A hepatic cell line showed improved drug metabolism as enzymatic activity of a number of different CYPs where increased when cultured as spheroids in alginate compared to in 2D monolayer cultures (Elkayam, T. et al., 2006). Recently several new products for providing 3D scaffolds to support cell culture have been launched on the market, including 3D interweaving nanofibre scaffolds which have been found to improve hepatic culture conditions (Wang, S. et al., 2008). Alternatively, porous polystyrene scaffolds provides space to enable cells to grow and differentiate and form layers that develop complex 3D cell-cell interactions (Bokhari, M. et al., 2007a; Bokhari, M et al., 2007b). In these scaffolds, HepG2 respond to biochemical agents in a manner much more resembling the activity of tissues in vivo compared to cultured in 2D (Bokhari, M. et al., 2007a). Additionally, mouse ES cells have successfully been differentiated as spheroids in perfused polyurethane foam towards hepatocytes, aiming to develop a mass differentiation culture method by combining growth factor treatment with multicellular spheroid formation (Matsumoto, K. et al., 2008).

Hepatocyte Cell Culture

Liver failure and end-stage liver diseases are responsible for a huge amount of deaths around the world and is a major burden on the health care system. Liver transplantation remains the most successful treatment. However, the efficacy of this procedure is limited and connected to many complications such as infection or rejection. Liver transplantation also suffers from shortage of available donor organs and the treated patients will very often be referred to lifelong immunosuppression therapy. By reducing the need for organs, cell-based treatment will be of great importance to both society and to the individuals suffering from these severe diseases.

Furthermore, the liver is the centre of metabolism and detoxification in the human body, and therefore huge efforts have been undertaken in order to identify a reliable source of functional cell types for in vitro testing. Unfortunately, the complexity and function of the liver is not mirrored by any cell type available today.

Methods for generation of hepatocyte-like cells from hPS cells, which may be further differentiated into mature hepatocytes, often includes the formation of embryoid bodies and/or early selection based on addition of cytotoxic compounds (Rambhatla, L. et al., 2003). These selection steps, especially formation of embryoid bodies, often results in a major cell number loss and in turn low efficiency. The methods are complicated, most having very long generation times and involve several time consuming steps. Thus, there is a need for rapid and simple method for the formation of hepatocyte-like cells derived from undifferentiated hBS cells. Previous attempts to obtain hepatocyte-like cells as e.g. published in US 20030003573 results in a low yield in relation to the starting material. Furthermore, the availability of primary human liver cells is very limited and the cells are also known to rapidly loose their normal phenotype and functional properties when used for in vitro applications. One often used alternative to primary cells are hepatic cell lines which in turn contain very low levels of (or totally lack) metabolising enzymes and have distributions of other important proteins substantially different from the native hepatocyte in vivo. Thus, many tests are still performed using animal material, even though liver metabolism is known to be species specific and thereby generating difficulties in predicting liver metabolism and toxicity in other species than the one tested.

In pharmaceutical development, adverse liver reactions remain the most prominent side effect. Therefore early prediction of human liver toxicity liabilities is of paramount importance when selecting compounds to enter clinical trials. Efforts to improve capabilities in this area must address both the availability question and development of models, which provide greater coverage for the complex biological processes which coincide to induce adverse liver injury in humans.

Accordingly there is an urgent need for a model system that mimics human liver cells and that is able to predict effects of candidate molecules in the development of new drugs or chemicals. Regarding both availability and physiological relevance, hPS cells may serve as an ideal renewable source of functional human hepatocytes.

SUMMARY OF THE INVENTION

The inventor of present invention has established a number of robust protocols which allow for the seeding of either hPS cells, hepatocyte precursors or hepatocyte progenitors onto 3D bioscaffolds to reproducibly and scalably give rise to hepatocytes with a mature morphology and function.

The invention comprises a method for improving the differentiation of human pluripotent stem cells (hPS) into hepatocyte progenitor or hepatocyte cell types, whereby the hPS cells are initially cultured on a 2-dimensional culture surface before being transferred to one of a defined set of 3D bioscaffolds for further differentiation and maturation. hPS cells may also initially be partially differentiated on a 2-dimensional surface into hepatocyte progenitor cell types. Subsequently, hepatocyte progenitors or hPS cells are seeded either onto a naked 3-dimensional scaffold or a scaffold which has been coated with a matrix compound and further cultured.

As an important aspect of the invention, the inventors have found that by initially growing and optionally initially differentiating hPS cells in a 2D environment before transferring the cells to a 3D environment significantly increases the expression of hepatocyte associated genes and the production of hepatocyte associated enzymes.

DEFINITIONS

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson, J. A. et al. (1998), Heins, N. et. al. (2004), as well as induced pluripotent stem cells [see, e.g. Yu, J. et al., (2007); Takahashi, K. et al. (2007)]. The various methods and other embodiments described herein may require or utilise hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein "hiPS cells" (also "iPS") refers to human induced pluripotent stem cells.

As used herein "definitive endoderm (DE)" and definitive endoderm cells (DE-cells) refers to cells exhibiting such as but not limited to protein or gene expression and or/or morphology typical to cells of the definitive endoderm or a composition comprising a significant number of cells resembling the cells of the definitive endoderm.

As used herein, "hepatic precursors", "hepatic progenitors" or "hepatic progenitor cells" refers to cells exhibiting markers such as but not limited to protein or gene expression and/or morphology typical to cells of the definitive endoderm or a composition of cell comprising a significant number of cells resembling the cells of the hepatic precursors or hepatic progenitors.

As used herein, "hepatocytes" or "hepatocyte-like cells (HCLC)" is intended to mean a cell type which is expressing at least some mature hepatic markers such as Albumin, CYP3A4, UGT2B7, OATP-2, ADH1A, UGT1A6, CYP2C9, CYP2C19 and CYP2D6.

As used herein, "hESC-HEP" is intended to mean a cell type derived from human embryonic stem cells which is expressing mature hepatic markers such as Albumin, CYP3A4, UGT2B7, OATP-2, ADH1A, UGT1A6, CYP2C9, CYP2C19 and CYP2D6.

As used herein, "hiPS-HEP" is intended to mean a cell type derived from induced pluripotent stem cells which is expressing mature hepatic markers such as Albumin, CYP3A4, UGT2B7, OATP-2, ADH1A, UGT1A6, CYP2C9, CYP2C19 and CYP2D6.

As used herein, "Xeno-free" refers to a cell line or cell material which has never been exposed to, directly or indirectly, material of non-human animal origin, such as cells, tissues and/or body fluids or derivatives thereof.

As used herein, "Wnt-signalling" refers to the pathways included in the Wnt signalling as reviewed in, e.g. Nejak-Bowen and Monga (2008).

As used herein HDAC inhibitors refers to Histone deacetylase inhibitors.

As used herein, "GSK inhibitor" refers to a compound which inhibits GSK (especially GSK3, including GSK3alpha or GSK3beta). Examples of preferred GSK inhibitors for use in the present invention include one or more of the following: BIO (2'Z,3'E)-6-Bromoindirubin-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(l-pyridyl)[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(l-(3-Hydroxypropyl)-lH-pyrrolo[2,3-b]pyridin-3-yl]-4-pyrazin-2-yl-pyrrole-2,5-dione (GSK-3beta Inhibitor XI); TWSI 19 pyrrolopyrimidine compound (GSK3beta Inhibitor XII); L803 H-KEAPPAPPQSpP-NH2 or its Myristoylated form (GSK3beta Inhibitor XIII); and 2-Chloro-l-(4,5-dibromo-thiophen-2-yl)ethanone (GSK3beta Inhibitor VI); and Aminopyrimidine CHIR99021. In addition, numerous wingless proteins or Wnt proteins function similar to GSK inhibitors and in particular, GSK inhibitors according to the present invention. They are therefore subsumed under the term GSK inhibitors. Exemplary Wnt proteins which may be used in the present invention include one or more of Wnt1, Wnt2, Wnt3, Wnt3a, Wnt4, Wnt10, Wnt 14, Wnt14b, Wnt15, and Wnt16, among other Wnt proteins. The use of Wnt3a is preferred.

Furthermore small molecules can be used to direct Wnt-signalling. As well GSK36 blockers or inhibitors for Wnt-signalling induction can be used for modulation of Wnt-signalling to achieve directed differentiation and maturation. The Wnt-signalling pathway can be induced at a later stage after initiation or before induction occurs.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

As used herein, the term "GST" is intended to mean glutathione transferase, and examples of subtypes thereof are GST A1-1, GST M1-1, and GST P1-1.

As used herein the term "UGT" is intended to mean uridine diphosphoglucuronosyltransferase, which is a group of liver enzymes catalyzing glucuronidation activities As used herein, the term "Cytochrome P450 reductase" (also known as CPR) is intended to mean a protein which physiological function is the reduction of Cytochrome P450 enzymes by electron transfer and which is therefore required for Cyotchrome P450 enzyme-mediated reactions.

By the term "functional drug metabolising enzymes" is intended to mean functional enzymes belonging to the phase I and phase II enzymes that perform chemical modifications of xenobiotics and drugs, so called drug or xenobiotic metabolism.

As used herein, the term "functional activity" means effective measurable hepatic cell function, such as a measurable transportation of drugs for drug transporters and a measurable metabolism of enzymes for the Cytochrome P450s (CYPs), commonly detected in primary human hepatocytes.

As used herein, the term "extraembryonic endoderm (E×E)" is intended to mean the differentiated endodermal cells that, as to the opposite of the definitive endoderm, will constitute the compartments outside the embryo in the human development, such as the yolk sac.

As used herein, the term "AAT" is intended to mean the liver marker alpha-anti-trypsin.

As used herein, the term "Alcohol dehydrogenase 1" is intended to mean a type of dehydrogenase enzyme that facilitates the interconversion between alcohols and aldehydes or ketones with the reduction of NAD+ to NADH. Alcohol dehydrogenase 1 serves to break down alcohols which could otherwise be toxic.

As used herein, the term "AFP" is intended to mean the liver marker alpha-fetoprotein. As used herein, the term "BSEP" is intended to mean the bile transporter bile salt export pump.

As used herein, the term "CK" is intended to mean the liver marker cytokeratin (used interchangeably) with different subtypes such as Cytokeratin 18 (CK18/KRT18), Cytokeratin 19 (CK19/KRT19), Cytokeratin 8 (CK8) and Cytokeratin 7 (CK7).

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "BMP" means Bone Morphogenic Protein, preferably of human and/or recombinant origin, and subtypes belonging thereto are e.g. BMP4 and BMP2.

As used herein, the term "HGF" means Hepatocyte Growth Factor, preferably of human and/or recombinant origin.

As used herein the "HNF3beta", or "HNF3b", used interchangeably are intended to mean hepatocyte nuclear factor 3, a transcription factor regulating gene expression in endodermal derived tissue, e.g. the liver, pancreatic islets, and adipocytes. HNF3beta may sometimes also be referred to as HNF3b or Fox2A the latter name originating from the transcription factor being a member of Forkhead box transcription factors family.

As used herein the term "OCT-1" is intended to mean organic cation transporter 1. OCT-1 is a major hepatic transporter that mediates the uptake of many organic cations from the blood into the liver where the compounds may be metabolized or secreted into the bile.

As used herein the term "MDR" is intended to mean multidrug resistance transporter. MDR 1 and 3 are members of the ATP-binding cassette (ABC) family of transporters and both are drug efflux transporters. MDR 1 is important in regulating the traffic of drugs, peptides and xenobiotics into the body and in protecting the body against xenobiotic insults and drug toxicity, while MDR 3 is essential for phospholipid secretion into bile.

As used herein the term "Activin" is intended to mean a TGF-beta family member that exhibits a wide range of biological activities including regulation of cellular proliferation and differentiation such as "Activin A" or "Activin B". Activin belongs to the common TGF-beta superfamiliy of ligands.

As used herein the term "ROCKInhibitor" is intended to mean a small molecule inhibitor of the ROCK Rho-kinase, such as Y-27632 or Fasudil.

As used herein the term "xeno-free" is intended to mean complete circumvention of direct or in-direct exposure to non-human animal components.

As used herein, the term "hepatocellular toxicity" indicates cellular responses such as necrotic toxicity, apoptosis, mitochondrial toxicity, phospholipidosis, steatosis and bile acid transport.

DETAILED DESCRIPTION OF INVENTION

One aspect of the present invention relates to a method for differentiating human pluripotent stem cells (hPS) or hepatocyte precursor cells into mature hepatocyte or hepatocyte-like cells, the method comprising the steps:

i) Seeding of hPS or hepatocyte precursor cells on a 2-dimensional surface to initiate differentiation ii) Transferring the initially differentiated cells of step i) to a 3-dimensional (3D) scaffold for further differentiation and maturation.

The cells may be seeded at a higher density on the 3D scaffolds than on the 2D cultures, such as threefold higher or fivefold higher or tenfold higher however. Further, Rho kinase (rock) inhibitors may be added and/or the method can be performed under feeder-free or xeno-free conditions.

The cells used in the methods according to present invention may be xeno-free cells, such as a xeno-free hPS cell line or cells derived from a xeno-free hPS cell line, or the cells may be human embryonic stem (hES) cells or induced pluripotent stem (iPS) cells. The hepatocyte precursor cells according to present invention may be definitive endoderm (DE) cells or not and may have characteristics of fetal endoderm or hepatic endoderm.

The transition from step i) and ii, i.e. the transfer of the cells obtained in step i) are transferred to a 3D-scaffold (step ii) may be performed after 2 to 25 days, such as 4 to 15 days.

The 3 dimensional scaffold may be chosen from one of the following types: i) a porous alginate sponge, ii) a biodegradable poly (urethaneurea) (PUUR) polymer, iii) an emulsion-templated polystyrene, iv) a synthetic nanofibrillar composite v) a microwell device with at least one non-vertical side-wall, vi) a porous sponge fabricated from Poly (L-lactic Acid) [PLLA] or the 3 dimensional scaffold may be of another suitable type.

The porous alginate sponge may have a pore size of 50-200 μM, whereas the pore size of the emulsion templated polystyrene scaffold is in the range of 0.1-1000 μM, such as 15-45 μM.

Further, present invention relates to a method as described above, wherein the 3D-scaffold is uncoated. In another aspect, the 3D-scaffold is pre-coated e.g. with one or more extracellular matrix components. Examples of such extracellular matrix components comprise: gelatine, laminin, fibronectin, collagen, polylysine, vitronectin, hyaluronic acid, hyaluronan hydrogels, silk fibroin, chitosan or a composite of any of the forementioned.

The 3D-scaffold of present invention may be contained within a suitable culture vessel, such as a multiwell plate including but not limited to a 6-well plate, a 12-well plate, a 24-well plate, a 48-well plate, a 96-well plate, a 384-well plate, a 1536-well plate or other suitable cell culture vessel.

Hence, the invention detailed herein comprises a process used to improve the differentiation of hPS cells towards cells having a more hepatic phenotype or cells ultimately having a partially or fully mature hepatic phenotype, this process requiring the cells to be initially cultured on a 2-dimensional culture surface before being transferred one of six possible 3-dimensional scaffolds. This improvement in hepatic phenotype is independent of any particular cell culture medium composition (see FIG. 9 for details of cell culture protocols employed).

Based on gene expression and metabolic studies, the inventors of the present invention have found that 3D scaffolds provide a better environment for the maturation and further differentiation of hPS-derived hepatocyte cells or hepatocyte progenitors compared to more traditional 2D substrates (FIGS. 1-6). Further, the inventors have found a further effect when culturing the cells on a 2D surface before seeding the cells in the 3D environment.

This can be seen by comparing the expression of several hepatic marker genes such as Cyp2C9, Albumin, Cyp3A4, and UGT2B7 which are all expressed more highly in cells cultured on 3D scaffolds than on 2D surfaces, regardless of cell line, matrix coating, days in culture or scaffold chosen.

Specifically, a large number of hepatic transporters (BSEP, FABP1, MRP2, NTCP, OATP2, OCT1) are expressed in much higher levels when cultured in 3D indicating more mature and functional hepatocytes. This can be seen for a range of different scaffold types including topographical scaffolds such as Ultraweb (FIG. 3) and Aggrewell (FIG. 5), porous sponge types such as AlgiMatrix (FIG. 2) and Poly-L-lysine (FIG. 6) and on synthetic polymer-based scaffolds such as Artelon (FIG. 1) and Alvatex (FIG. 4).

The 3D scaffold may be pre-coated with a matrix component to better resemble in vivo microenvironment normally encountered by hepatocytes. Specifically, the matrix components gelatine and matrigel have been shown to improve the expression levels of some hepatic markers when used in conjunction with the scaffolds. Expression of several markers (TAT, CYP2C9, OATP2,) is higher on matrigel-coated Artelon (Artimplant) compared to uncoated (FIG. 1 C & E; FIG. 1 A & D). A number of markers (TAT and UGT2B7) are significantly more highly expressed on matrigel-coated Alvatex compared to uncoated (FIG. 4 F & G, analysed at day 18) and this is also true for several other markers (such as TAT, UGT2B7) which are expressed to a higher degree on gelatine-coated Alvatex compared to uncoated (FIG. 4 E & G). This particular embodiment of the invention can be optionally applied depending upon which markers it is desired to see expressed to a high degree. Since expression of a particular set of markers will imply a certain phenotype or stage of hepatic lineage, application of this aspect of the invention may allow a finer degree of control over the functionality of the hepatocytes generated. An extension of this aspect could be the addition of one or more different cell types to the hPS cells or hPS-derived hepatic progenitors which are seeded onto the 3D scaffolds, allowing co-culturing of cell lines on the 3D scaffolds.

Notably, the cells may be seeded at different relative densities on the 3D scaffolds. The relative density may be a standard ×1 density (i.e. the same density as cells seeded on the 2D control surface) or a three-fold higher initial density (designated as x3) or a ten-fold higher density or any density there in between. FIG. 1 H & I show that expression of markers OATP2, OCT1 and TAT is higher in cells seeded at the lower x1 initial density when using uncoated Artelon (Artimplant). Expression of certain markers (e.g. CYP7A1) are also lower on cells seeded at ×3 on uncoated Alvatex compared to cells seeded at ×1, (FIGS. 4 N & O) but other markers (such as OCT1) had higher expression in cells seeded at ×3 on uncoated Alvatex (FIG. 4 I & K). Therefore application of this particular embodiment is again dependent upon the desired phenotype of the hepatocyte cells which is required by the user.

To permit control of the differentiation, the stage of differentiation at which the cells are seeded on the 3D scaffolds is relevant, i.e. cultured for longer being of a more mature phenotype before seeding in 3D scaffold. The hPS cells can be seeded in the scaffolds at several different stages of differentiation, e.g. as undifferentiated cells (day 0) or after treatment with activin A for definitive endoderm-induction (day 4-7) or as hepatic precursors (day 9, 11, 13, 14 and 15) for maturation in the 3D-scaffolds. Characterisation of such precursor cells can be carried out to determine that they are on embryonic endodermal lineage prior to seeding on scaffolds (FIG. 11) or the more advanced hepatocyte precursor (FIG. 12), based on expression of defined marker genes characteristic for both stages. Differences are readily observed on cells cultured on Artelon (Artimplant), where for example, expression levels of OCT1 are almost double in cells seeded at 14 days compared with those seeded at day 11 (FIG. 1 F & H). In contrast to this, levels of OATP2 are decreased in cells seeded at 14 days on Artelon (Artimplant) compared to those seeded day 11 (FIG. 1 J & M). This trend can also be seen in cells cultured on Alvatex, where again the 14 day old seeded cells possess lower expression levels of OATP2 than the 11 day cells, possibly indicating that OATP2 is a marker for more immature hepatocyte phenotypes (FIG. 4 I & J). In a similar manner it can be seen that levels of OCT1 are also higher in cells seeded when younger (day 11) than in more mature (day 14), (FIG. 4 N & P). Thus length of cell culture and differentiation time is an important factor of this invention in terms of controlling final phenotype of the cells produced and can be altered accordingly. As outlined in FIG. 9, and in the table below, the duration of culturing and the media compositions may be adjusted to optimize the maturity and developmental stage of the cells obtained by the methods disclosed herein. A related aspect concerns the differentiation regime to which the cells are subjected prior to seeding onto the scaffolds, as detailed in Example 2, in particular whether the cells are exposed to medium containing an inhibitor of the Rho-kinase ROCK, such an inhibitor being used to improve survival and re-attachment of cells after passaging and seeding both in the 2D and 3D stages.

An improvement in function and metabolic activity has been observed in the hepatocytes seeded onto 3D scaffolds compared to those grown on conventional 2D surfaces. hESC-derived hepatocytes, matured in 3D scaffolds according to Example 6, showed greater induction of CYP activity than 2D control cultures (FIGS. 7 & 8, 10) when exposed to the drugs Phenacetin (APAP), Midazolam or Diclofenac, with the Alvatex scaffold showing the greater induction than the Ultraweb. A further examination of cells cultured on Alvatex (Reinnervate) showed that at both 23 and 29 days after initiating differentiation, those cells had a much greater metabolic activity than cells cultured on 2D surfaces as measured by CYP2C9 activity. CYP2C9 activity was already high in cells cultured on 3D surfaces but was also observed to be elevated when cells were treated with diclophenac (FIG. 8). This again shows that hepatocytes which are differentiated on 3D scaffolds have a superior metabolic hepatocytoc function when compared to 2D cultured cells. These results are borne out by the findings that levels of the crucial hepatic marker CYP3A are also higher in cells cultured on matrigel-coated Alvatex (Reinnervate) and slightly higher in cells cultured on Ultraweb compared to the 2D control when cells were assayed for metabolic breakdown products of the drug Midazolam (FIG. 8). Thus the invention has shown several examples of improved hepatic metabolic activity in cells cultured on 3D scaffolds.

Hence as discussed above an aspect of the present invention relates to a method wherein the hepatocyte cells or hepatocyte progenitors display elevated metabolic activity as shown by increased expression of one or more CYP markers, such as CYP2C9 or CYP3A and/or elevated levels of hepatocyte-associated genetic markers selected from the list comprising: CYP1A1, CYP1A2, CYP3A4, CYP2C9, CYP3A7, CYP7A1, MRP2, Albumin, UGT2B7, AAT, TAT.

Further, an aspect of present invention relates to a method wherein the hepatocyte cells or hepatocyte progenitors display increased expression of one or more hepatic-associated transporter proteins such as BSEP, FABP1, MRP2, NTCP, OATP2, OCT1.

The present method may as discussed above, stimulate that the proportion of hepatocytes or hepatocyte progenitors compared to non-hepatocyte cells is greater than 5%, such as 10%, such as 20%, such as 30%, such as 40%, such as 50%, such as 60%, such as 70%, such as 80%, such as 90%, such as 100%.

A method according to any of the preceding claims wherein the hepatocytes or hepatocyte progenitors are co-cultured on the 3D scaffolds with at least one other cell type chosen from, but not limited to: stellate hepatic cells, hepatic immune (Kuppfer) cells, hepatic endothelial cells, biliary epithelial cells or fibroblasts Accordingly and as discussed above, an aspect of the present invention relates to an hPS derived hepatocyte cell or hepatocyte progenitor cell or a composition comprising an hPS derived hepatocyte cell or hepatocyte progenitor cell obtainable by a method described herein. Further aspects of the present invention relates to the use an hPS derived hepatocyte cell or hepatocyte progenitor cell or a composition comprising an hPS derived hepatocyte cell or hepatocyte progenitor cell obtained by the methods herein in therapy, regenerative medicine, for drug screening, toxicity testing or drug delivery.

The composition may further comprise a 3D scaffold, such as but not limited to a porous alginate sponge, a biodegradable poly(urethaneurea) (PUUR) polymer, an emulsion-templated polystyrene or a synthetic nanofibrillar composite.

EXAMPLES

Example 1

Starting Material for Hepatocytes Derived from Human Pluripotent Stem Cells

All hPS cells (as defined above) can be used as staring material for this invention. For the examples below hepatocyte-like cells were derived in vitro from undifferentiated human embryonic stem cells (hESC) cultured on mEF cells (Heins, N. et al. 2004, Stem Cells). The cell lines used for this experiment could be, but is not limited to the hES cell line SA002, SA121, SA181, SA461 (Cellartis AB, Göteborg, Sweden, http://www.cellartis.com) and they can be propagated as described Heins, N et al. 2004. These cell lines are listed in the NIH stem cell registry, the UK Stem Cell bank and the European hESC registry and are available on request. Along with hPS obtained from hESC, hPS obtained from hiPS (induced pluripotent stem cells) have been used for the derivation of hepatocytes for the examples of this invention. In this case, "hiPS-HEP" is intended to mean a cell type derived from induced pluripotent stem cells which is expressing mature hepatic markers such as Albumin, CYP3A4, UGT2B7, OATP-2, ADH1A, UGT1A6, CYP2C9, CYP2C19 and CYP2D6 (see also "Definitions"). Use of xeno-free iPS cells or a xeno-free derived hES cell line such as SA611 (Cellartis AB, Goteborg, Sweden, http://www.cellartis.com) could optionally allow the entire invention to be used under xeno-free conditions to produce a xeno-free cell product.

Example 2

Derivation of Hepatocytes from Human Pluripotent Stem Cells Using 3D Scaffolds.

Hepatocytes were derived from both hES cells and human hiPS cells according to the protocols a-e, as detailed below. Before start of differentiation, the cultures were washed twice with PBS. The different media (Table 1) were prepared freshly and added from day 0 and afterwards according to the protocol overview. Medium was changed every day or every second day during the initial differentiation (ID) step, and every second or every third day afterwards. Only one cell line was used for each experiment, but optionally a second (or more) cell line could be added when the initial cell line is seeded onto the 3D scaffolds allowing co-culturing of the cells.

2D cultures were seeded on matrigel coated culture vessels, except in experiment 114 and 116 when 2D cultures were seeded on gelatin coated culture vessels. 2D cultures were seeded in 150.000-200.000 cells/cm$^2$.

The table below shows an overview of the different experiments, which cell lines were used as starting material, the variants of differentiation protocol as outlined in FIG. 9, time of the differentiation protocol when the cells were seeded in 3D scaffolds, time of differentiation when cells were analyzed, and whether 10 mM ROCKInhibitor was added or not to the medium at time of seeding in scaffolds (see also FIG. 9 for schematic details of protocols employed):

| Experiment no. | Protocol (see FIG. 7) | Cell lines | Seeded in 3D | Analyzed | ROCK-Inhibitor |
|---|---|---|---|---|---|
| Exp083 | e | SA461FF | Day 15 | Day 30 | − |
| Exp088 | d | SA002ECD | Day 14 | Day 24 | − |
| Exp089 | d | SA002ECD | Day 14 | Day 24 | − |
| Exp098 | c | SA002DEF SA181DEF SA461DEF | Day 5 | Day 25 | − |
| Exp104 | b | SA121DEF | Day 4 | Day 18 & 22 | − |
| Exp112 | a | SA121DEF SA181DEF | — | Day 7 | − |
| Exp113 | a | SA181DEF | Day 11&14 | Day 24 | + |
| Exp114 | a | SA181DEF | Day 9, 11 & 14 | Day 24 | + |
| Exp116 | a | SA121DEF | Day 13 | Day 24 | + |
| Exp118 | a | SA181DEF | Day 0, 7, 11 | Day 24 | + |
| Exp119 | a | SA121DEF SA181DEF | Day 0, 7, 11 | Day 24 | + |
| Exp120 | a | SA181DEF | Day 0, 7, 11 | Day 24 | + |
| Exp122 | a | SA121DEF | — | Day 7 | − |
| Exp139 | g | SA121DEF | Day 7 | Day 24 | − |
| Exp140 | g | SA121DEF | Day 7 | Day 24 | − |
| Exp148 | g | SA121DEF | Day 7 | Day 24 | − |
| Exp153 | i | SA121DEF | Day 4 | Day 25 | − |
| Exp169a | h | IMR90 | Day 7 | Day 7 and day 32 | + |
| Exp169b | f | IMR90 | Day 4 | Day 4 and day 29 | + |
| Exp172 | f | IMR90 | Day 7 | Day 29 | + |
| Exp175 | g | SA121DEF | Day 11 | Day 25 | + |
| Exp175 | f | SA181DEF | Day 11 | Day 25 | + |
| Exp177 | g | SA121 | — | Day 11 | − |
| Exp177 | h | SA181 | — | Day 11 | − |
| CYP3A induction | g | SA121 | Day 7 | Day 24 | − |
| CYP3A induction | h | SA181 | Day 7 | Day 24 | + |

Example 3

Scaffolds

Scaffolds and Matrix Coatings Used in the Studies

Artelon (Artimplant); <150 μm poresize, formatted for 48 well plates, kindly provided by Artelon (Artimplant) (Västra Frölunda, Sweden) [see WO0035507; also Blumenthal, B. et al. (2010)]

Alvatex; size for 48 wells, kindly provided by Stefan Przyborski ReInnervate, (Durham, UK) (see WO07125288, WO10038013)

AlgiMatrix; Invritogen/Gibco, cat no 12684, lot nr 731950, 96 wells (exp088+089) [see WO08112904; also Shapiro, L & Cohen, S. (1997)]

UltraWeb; Corning, cat no 3873xx, lot no 09207043, 96 wells (exp088+089) [see WO09032117; WO10060066, also Piryaei, A. et al. (2010)]

Aggrewell; Stem Cell Technologies, cat 27865, approx. 300 microwells, [see WO2008106771]

HAC/Porocell; (HacBiomed); [Cell Transplant. 1997 September-October; 6(5):463-8.

Highly porous polymer matrices as a three-dimensional culture system for hepatocytes.

Kaufmann P M, Heimrath S, Kim B S, Mooney D J.]

Preparation of 3D Scaffolds and 2D Culture Dishes Before Use:

The Artelon (Artimplant) and Alvatex scaffolds were soaked in 70% EtOH, the EtOH was removed and the scaffolds were washed twice with DPBS.

Matrigel: Growth factor reduced matrigel from BD, Lot no 0934 was diluted to 0.016 mg/ml in DPBS, and added to scaffolds and 2D culture dishes, incubated at RT for at least 1 h RT, then matrigel was removed immediately before use.

Gelatine: gelatin from production was added to the scaffolds and/or 2D culture dishes, incubated at RT for at least 30 min, then the gelatin was removed immediately before use.

Example 4

Passaging and Maintenance of hES Cell Cultures

Media was removed from the cell cultures, and the cultures were washed 2× in DPBS−/− (37° C., 0.5 ml/cm$^2$). TrypLE Select was added (RT, 0.1 ml/cm$^2$) and incubated at 37° C. (4-5 min for undifferentiated cells or cells after Activin A treatment, 10-45 minute for cells at progenitor stage). The cells were then detached by flushing the cells with a p1000. VitroHES was added (37° C., 0.1 ml/cm$^2$) and the cell suspension was transferred to centrifuge tubes and centrifuged at 330×g 5 min at RT. The cell pellet was resuspended in culture medium, cells were counted and diluted to appropriate seeding suspension. In some experiments, 10 mM Rock inhibitor was added to the culture medium at day of seeding (exp113, 114, 116, 118, 119, 120)

Example 5

Gene Expression Analysis of hESC-Derived Hepatocytes Cultured on 3D Scaffolds.

hESC-HEP were derived from cell-line SA002, SA121, SA181, SA46 cultured from the DEF cultures system or SA002 cultures on mEF-layer as indicated in figure legends.

Total RNA was collected and isolated from the hES-HEP cultures at day 18, 22, 24, 25 and 30 by using RNA isolation kit from Qiagene. Quantitative reverse transcriptase PCR, QrtPCR, by using Taqman probes, was performed for the following hepatic marker genes: phase I drug metabolizing enzymes; CYP (cytochrome P450) 1A2, 2C9, 3A4, 7A1, phase II drug metabolizing enzymes GSTA1 (glutation-S-transferas A1), UGT2B7 (UDP glucuronosyltransferase 2B7), phase III, transporters; MRP2 (multi-drug residence protein 2, also called ABCC2), BSEP (bile salt export pump), NTCP (solute carrier, sodium/bile acid cotransporter) OCT1 (solute carrier, organic cation transporter), OATP2 (solute carrier, organic anion transporter), FABP1 (Fatty acid binding protein involved in fatty acid uptake, transport, and metabolism), and general hepatic markers; AAT (alpha-1 antitrypsin), ADH1A (alcohol dehydrogenase 1A) ALB (albumin) and TAT (tyrosine-amino transferas). All data was normalised to the house-keeping gene CREBBP, except when other is indicated. Data is presented as fold change of 2D controls, except when other is indicated.

Data is presented in FIGS. 1-4 and shows that hepatic genes are expressed at higher levels in hESC-HEP when cultured in 3D compared to 2D. The improved expression levels of the other hepatic markers in 3D cultures are supporting the finding that 3D cultures are important in hepatic differentiation of hESC.

Example 6

CYP Assay

At day 16, 18, 20, 21 and 25 hESC derived hepatocyte cultures were analyzed for cytochrome P450 1A, 2C and 3A activity by incubating the substrates Phenacetin, Diclophenac and Midazolam to a final concentration of 26 μM, 9 μM and 3 μM respectively in Phenol Red-free Williams Medium E, supplemented with 0.1% Penicilline-Streptomycin 2 mM L-Glutamine and 25 mM Hepes. A volume of 100 μl diluted substrates were added per cm$^2$ of the well surface (e.g. 75 ul pr 48 wells). hESC derived hepatocyte cultures with substrates were incubated over night. After 16 h, medium was collected and subsequently, centrifuged at 10 000 g, 4° C. for 20 min. Samples were analysed by Liquid chromatography-mass spectrometry (LC-MS) LCMS for presence of the metabolite Paracetamol, 4-OH-diclophenac and 1-0H Midazolam, biotransformed by the cytochrome p450 enzymes Cyp1A2, 1A1 (Phenacetin) Cyp 2C9, 2C8 (Diclophenac) and Cyp 3A4, 3A5 (Midazolam).

Example 7

Improved Cyp2C9 Activity and Improved Induction of CYP2C9 Activity in Cells Cultured in ReInnervate Scaffolds Cell line SA461 (Cellartis AB) was cultured and differentiated according to conditions in Examples 1 and 2, experiment 083 and then according to the scheme below:

| D0 | | Start of differentiation | | | Medium |
|---|---|---|---|---|---|
| D15 | 2D 24 well 7 wells | Relnn 24 well 7 wells | 2D 24 well 7 wells | Relnn 24 well 7 wells | Transfer to 3D and 2D |
| D16 | | | | | 50% medium change, M5 |
| D17 | | | | | 50% medium change, M |
| D18 | | | | | 50% medium change, M5 |
| D19 | | | | | — |
| D20 | | | | | 50% medium change, M5 |
| D21 | | | | | 50% medium change, M6 |
| D22 | Induction | Induction | | | induction |
| D23 | Activity assay start | Activity assay start | | | 100% medium change M6 |
| D24 | Activity assay finish, Resazurin & RNA | Activity assay finish, Resazurin & RNA | | | 50% medium change, M6 |

-continued

| | | | |
|---|---|---|---|
| D25 | | | 50% medium change, M6 |
| D26 | | | 50% medium change, M6 |
| D27 | | | — |
| D28 | Induction | Induction | 100% medium change M6 |
| D29 | Activity assay start | Activity assay start | 100%, 2.5 ml |
| D30 | Activity assay finish, Resazurin & RNA | Activity assay finish, Resazurin & RNA | 100% |

Growth medium composition as applied above:

| M5 | M6 | Spin down medium | Seeding medium |
|---|---|---|---|
| WME + SQ – GA1000 (+0.1% PEST) 2 ng/ml bFGF (0.2 μl stock/ml) 20 ng/ml HGF (2 μl stock/ml) | WME + SQ – GA1000 (+0.1% PEST) 10 ng/ml OsM (1 μl stock/ml) 0.1 μM DexM (1.6 μl stock/ml) 2 ng/ml bFGF (0.2 μl stock/ml) 2 ng/ml HGF (0.2 μl stock/ml) | 50% plating media from InVitroTech 50% WE | Seeding Media 50% Plating media from InVitroTech 50% M5 |

Differentiation was carried out up to day 15, and on Day 15 scaffolds were cut in small circles to fit into 24 well plates. The Alvatex (ReInnervate) scaffolds were washed with 70% EtOH, the EtOH was removed and the wells were washed twice with PBS+/+. Matrigel: GFR matrigel Lot no 6741 diluted to 0.016 mg/ml in DPBS, and added to scaffolds, 500 ul pr well and pr scaffold. The scaffolds were incubated for ~1 hour RT with the matrigel. The matrigel was removed immediately before use.

The aim was to seed in 2D wells with a split ratio of 1.5:1. In Alvatex (ReInnervate), 5 times as many cells were seeded, which is a split ratio of 7.5:1. Starting out with 27 wells of 9.6 $cm^2$, that is 260 $cm^2$. For seeding 100 ul pr $cm^2$ in the Alvatex (ReInnervate) scaffold the cells were resuspended in (260/7.5×0.1=34.6) 3.46 ml.

27 wells of cells were washed 1× in DBPS+/+ and 2 ml Tryple Select was added pr well, incubation 23 min at 37 C. The Spin down Medium was added and cells were flushed to detach them. Cells collected and spun 5 min 400×g. Resuspended in 3.46 ml Seeding Media. 200 ul of this suspension was seeded pr Alvatex (ReInnervate) scaffold. 600 ul of the suspension was diluted 5×, and of this, 200 ul was seeded pr 2D well. Then medium was added to a total of 800 ul pr well in all wells.

Counting cells: $27.9\times10^6$ cells/ml (87% viability), 3.46 ml total, $96\times10^6$ cells total.

| Scaffold | Well type | Area/ well | # wells seeded | Total area | Seeding volume/well | Cells/well seeded | Total medium volume per well |
|---|---|---|---|---|---|---|---|
| Alvatex (ReInnervate) 5× | 24 | 2 $cm^2$ | 14 | 28 $cm^2$ | 200 μl | $5.6 \times 10^6$ | 0.8 |
| 2D | 24 | 2 $cm^2$ | 14 | 28 $cm^2$ | 200 μl | $1.1 \times 10^6$ | 0.8 |

Induction:

Cells were induced with 1 mM Phenobarbital, 10 μM dexamethasone and 5 μM β-naphthoflavone.

To obtain these solutions 100 μl 64 mM dexamethasone solution was diluted with 540 μl DMSO to obtain a 10 mM dexamethasone solution 11.4 mg β-naphthoflavone was dissolved in 8.446 ml DMSO to obtain a 5 mM solution 1M Phenobarbital was diluted 1:1 with PBS To 35 ml M6 (w/o Dex) 35 μl 10 mM dex, 35 μl 5 mM β-naphthoflavone and 70 μl 0.5M Phenobarbital.

Control medium (non-induced medium) did not contain any DMSO to be able to compare the enzyme activity with the baseline enzyme activity.

To each well, either induction or control medium was added (400 ul/well 2D cultures, 2000 ul/well in ReInnevate scaffolds) and the plate was incubated 24 h.

Activity Assay:

After 24 hours of induction, all wells were washed 2× in DPBS+/+ and activity assay medium was added, 200 ul/well in 2D controls and 1000 ul/well in ReInnervate scaffolds. Activity assay medium: a protein-free medium without phenol red consisting of WE with 0.1% PEST, 2 mM L-Glutamine, 25 mm HEPES and 26 uM Phenacetin, 3 uM Midazolam and 9 uM Diclophenac.

After 16 hours incubation at 37 C, the medium was transferred to eppendorf tubes and spun down for 20 min at 4° C. and 10000 g. Supernatants were analyzed by HPLC for the presence of OH-Diclophenac, which is the metabolite of Diclophenac.

Example 8

Verification that Cells have Differentiated into Embryonic Endoderm or Hepatic Precursors at the Time of Seeding in the Scaffolds The protocols used for differentiation towards hepatocytes were analyzed for the formation of embryonic endoderm cells after the "endoderm induction" step, cells cultured according to protocol a) (FIG. 11). At day 7 in the differentiation protocol, cells were harvested for RNA and analyzed by Real-time PCR and compared to the undifferentiated cells from start of the experiment (day 0). It was shown that the differentiation protocols generated cells expressing embryonic endoderm markers (FOXA2, SOX17, HHEX, CXCR4, CER1). Furthermore, it was verified that markers (Nanog and OCT4) for undifferentiated cells was down-regulated compared to the undifferentiated starting material. Additionally, it was checked that cells were expressing extra-embryonic endoderm markers (Sox7 and CDX2), as these genes were not increased during the endoderm induction. A similar method was employed to test that cells which were being seeded onto scaffolds as "hepatic precursors" did indeed possess this phenotype (FIG. 12).

hESC-Derived Hepatocytes Cultured on Artelon (Artimplant))

Figure 1:
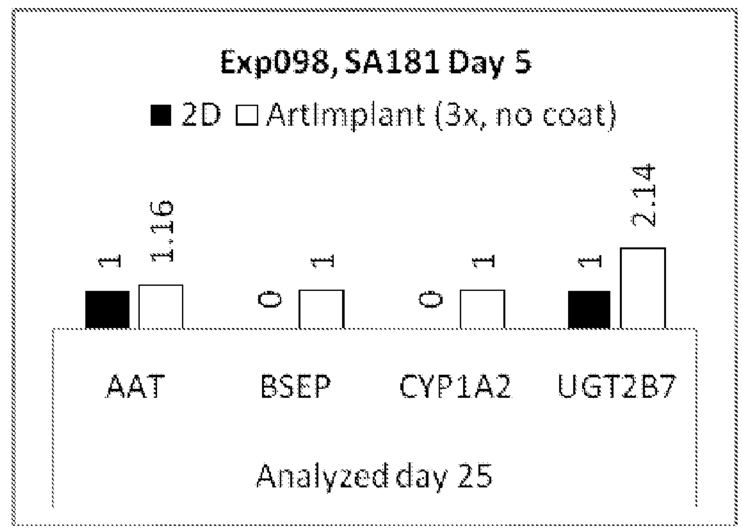
FIG. 1.
Figure 1:
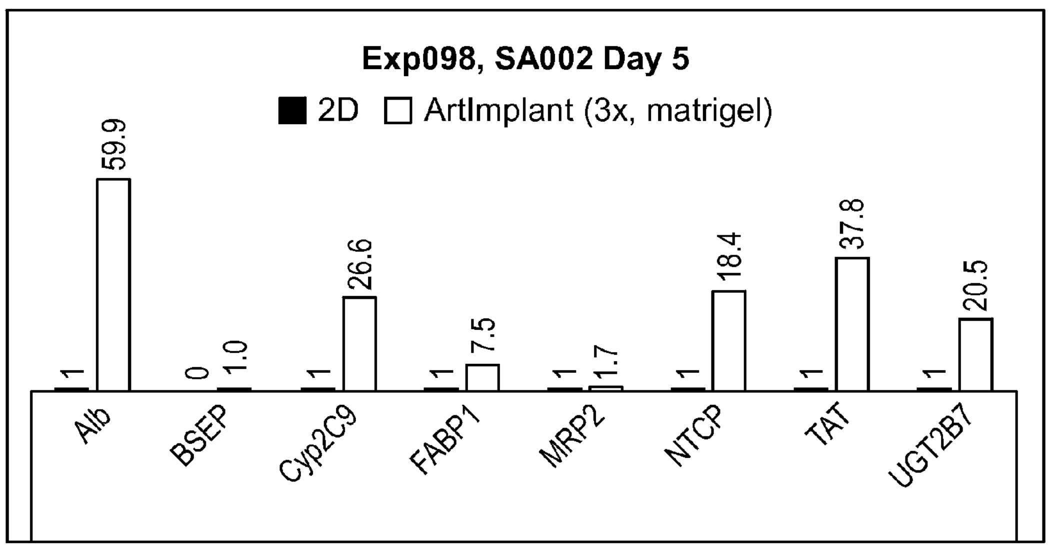
Figure 2A:
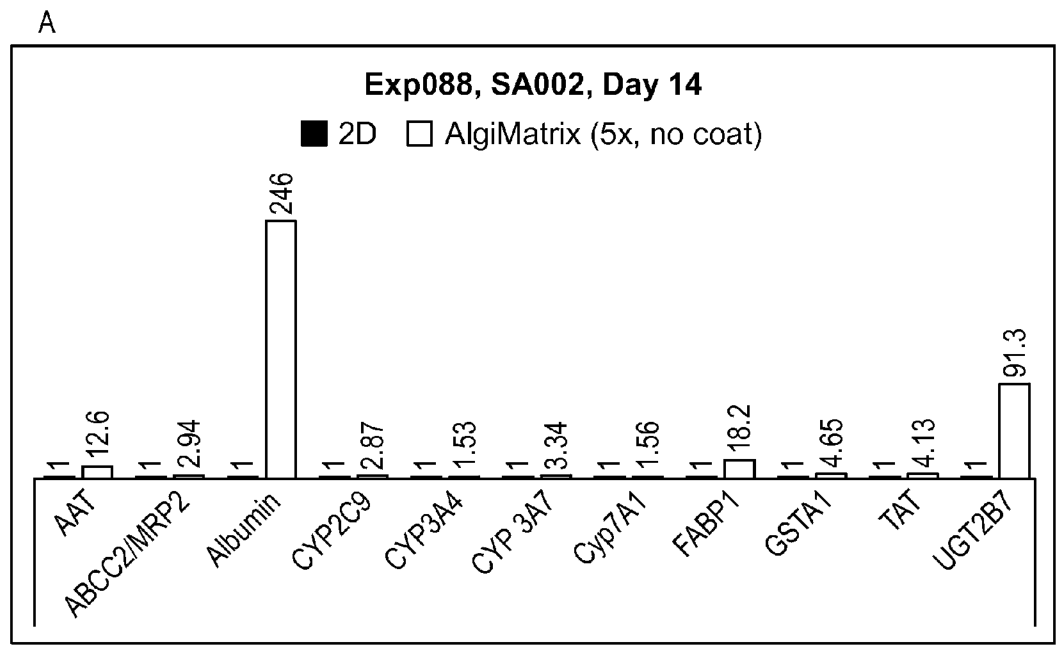
Figure 2A:
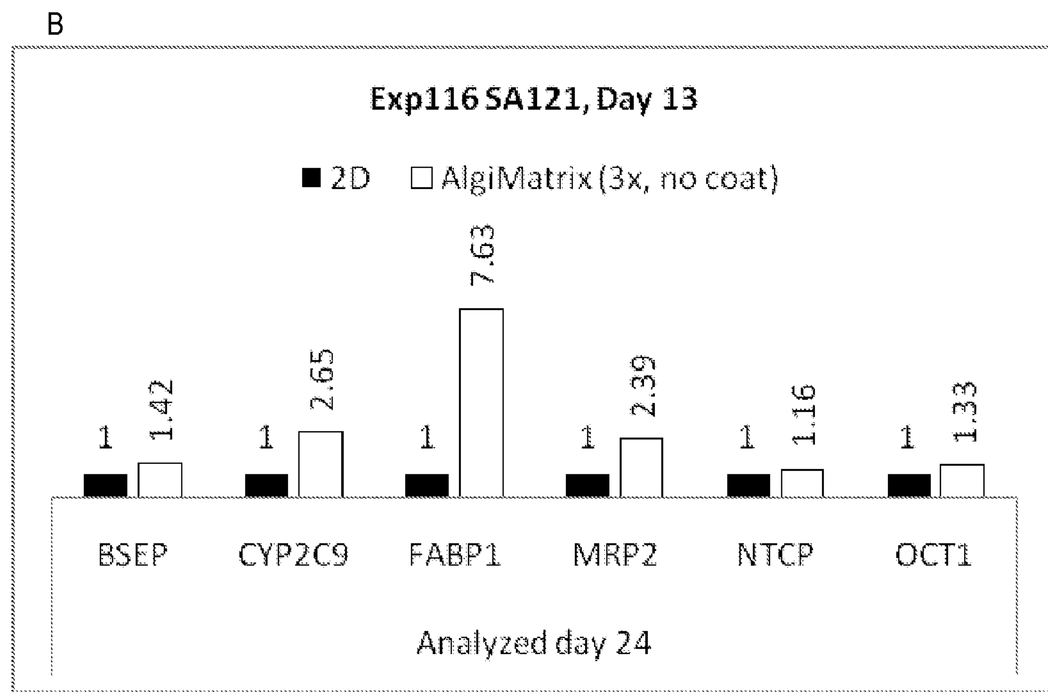
Figure 3:
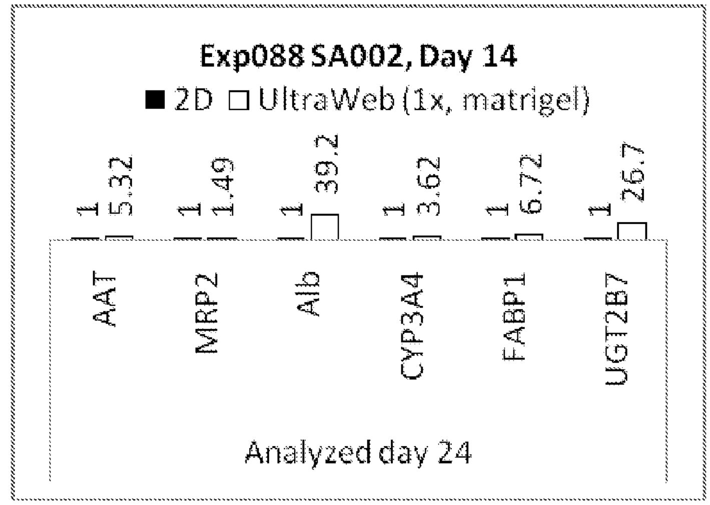
Figure 3:
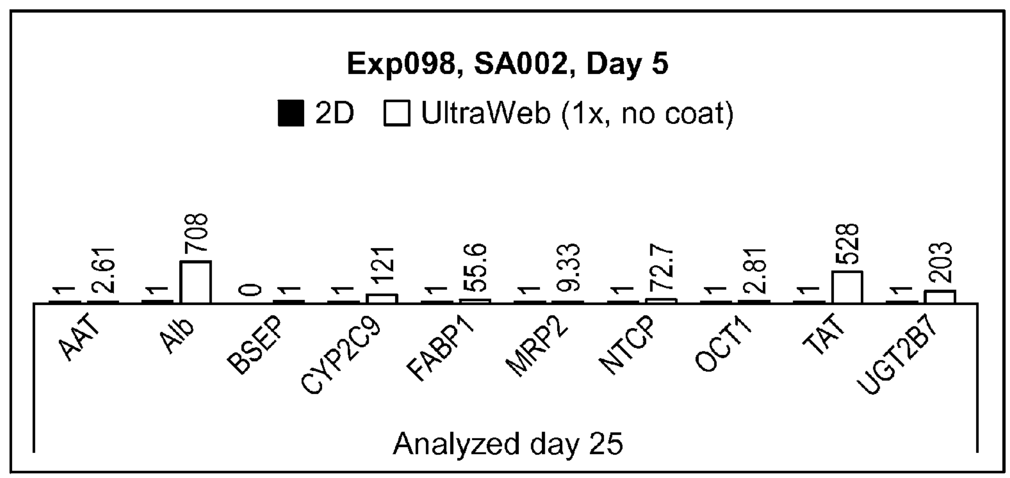
Figure 4A:
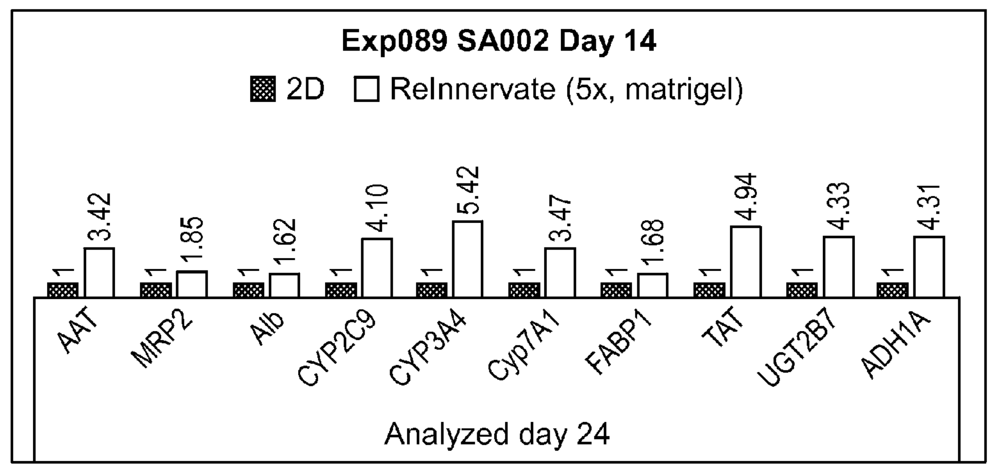
Figure 4A:
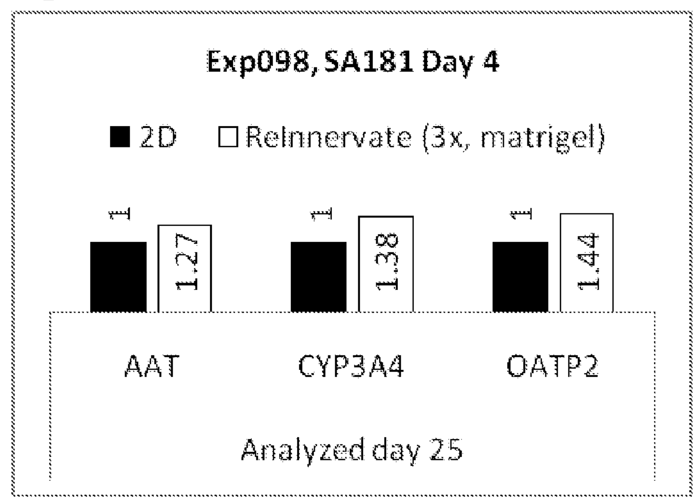
Figure 4B:
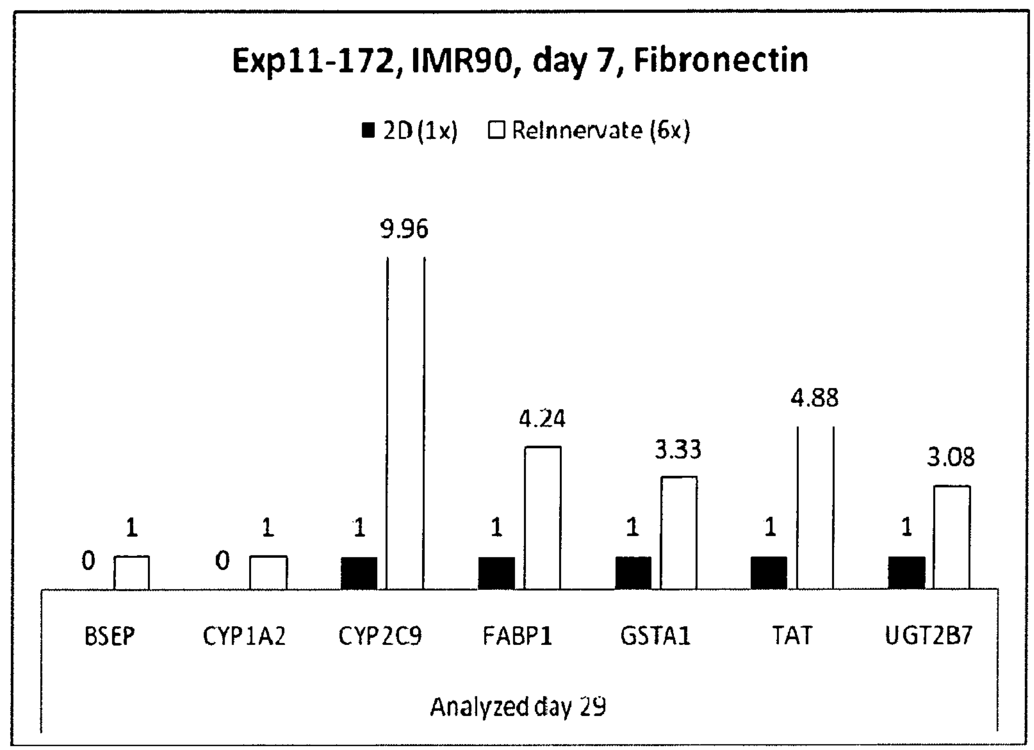
Figure 4B:
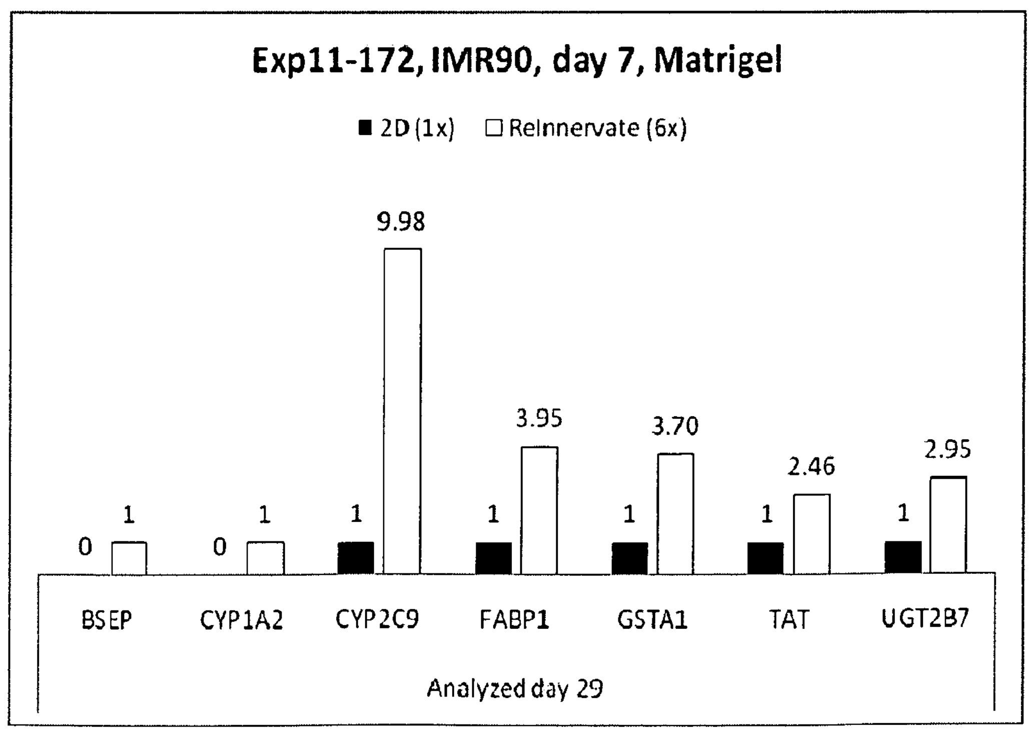
Figure 5A:
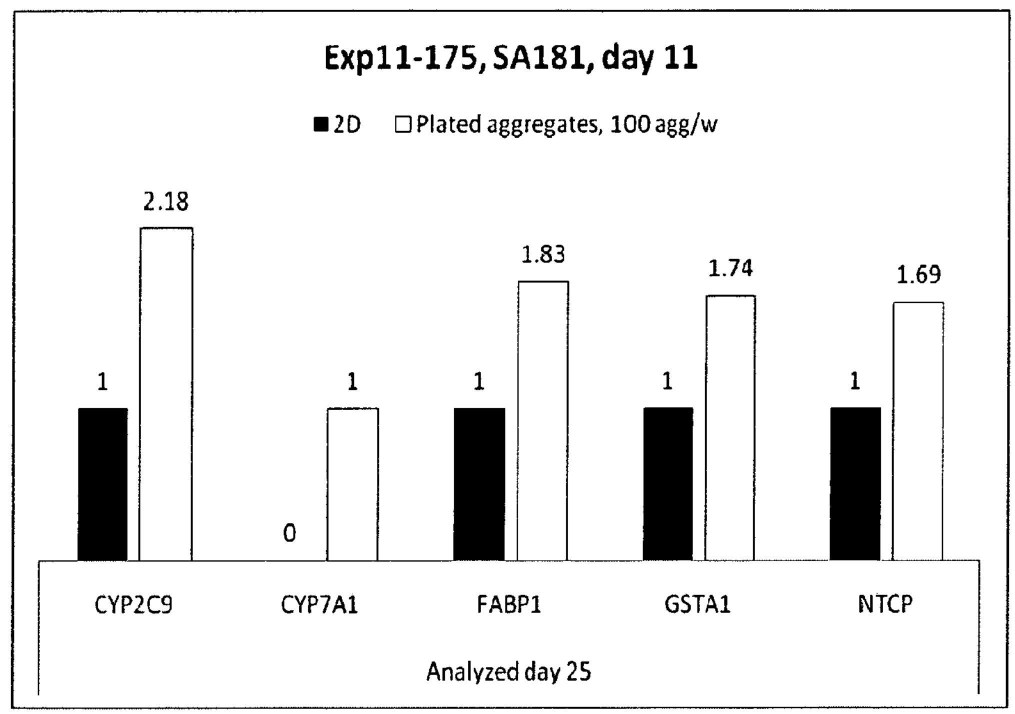
Figure 5A:
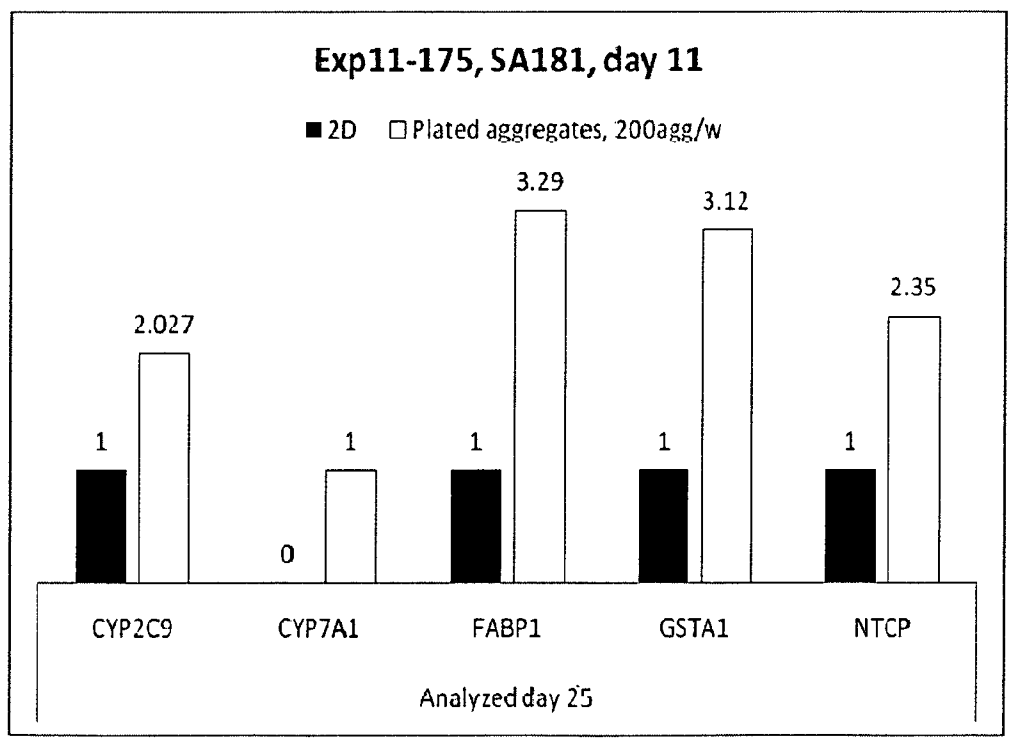
Figure 5B:
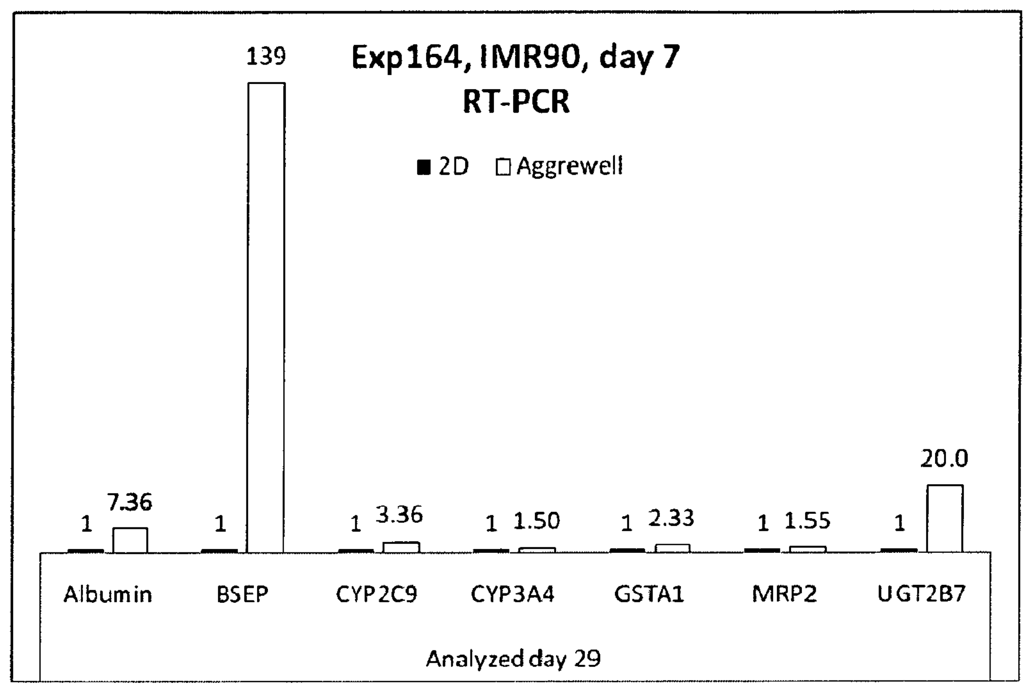
Figure 5B:
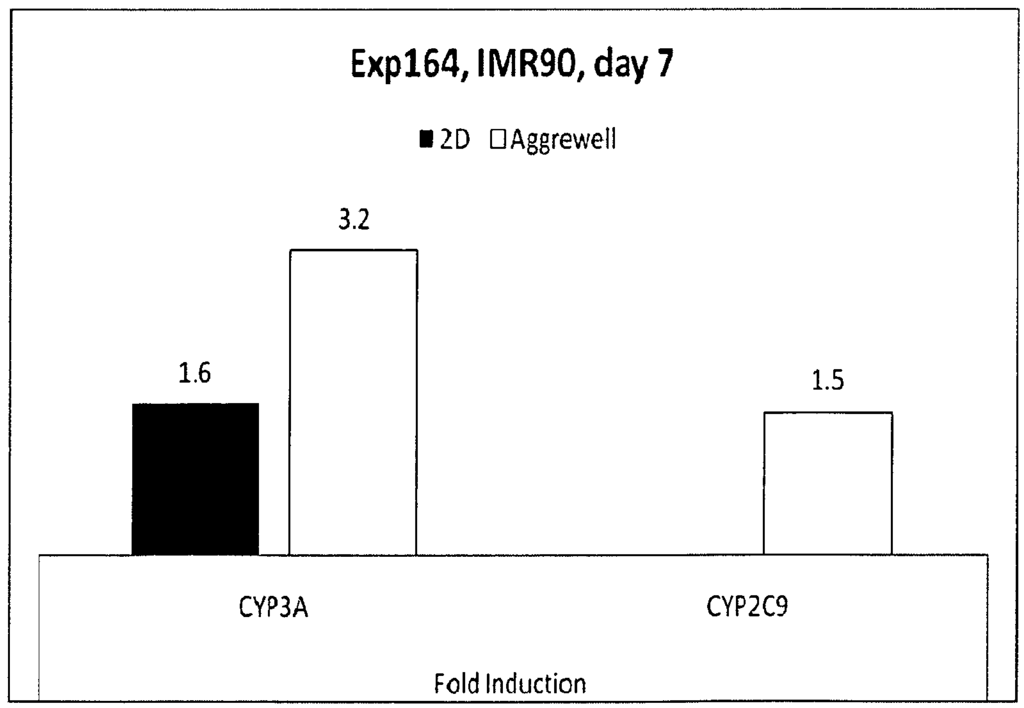
Figure 6:
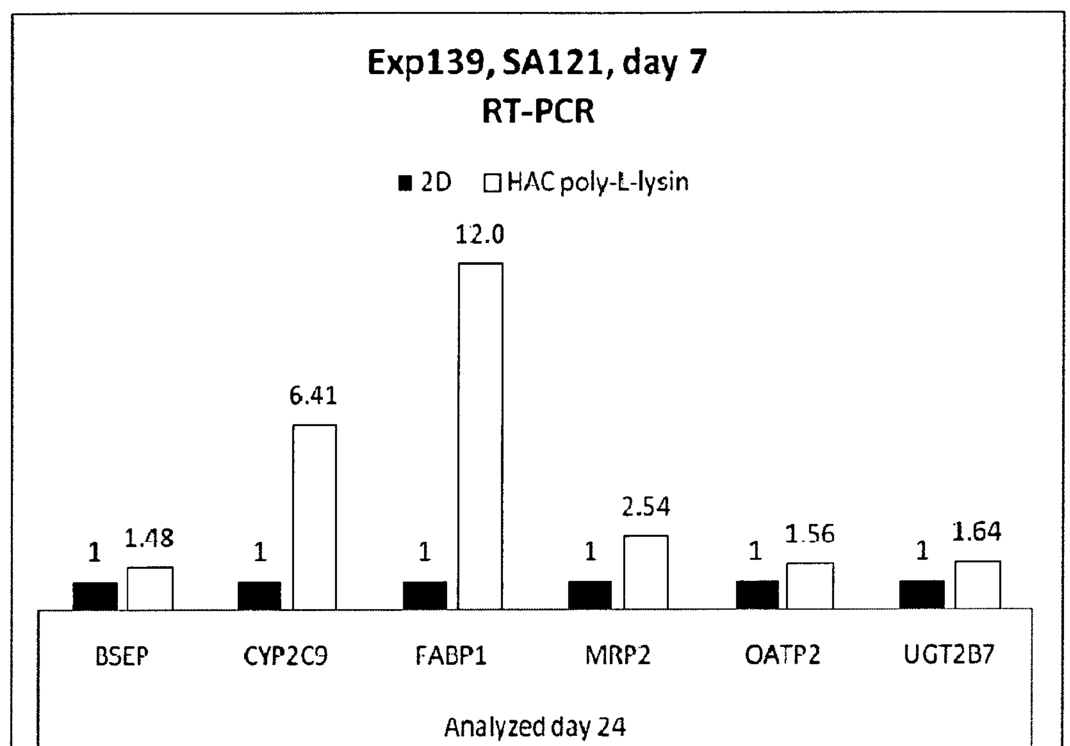
Figure 7:
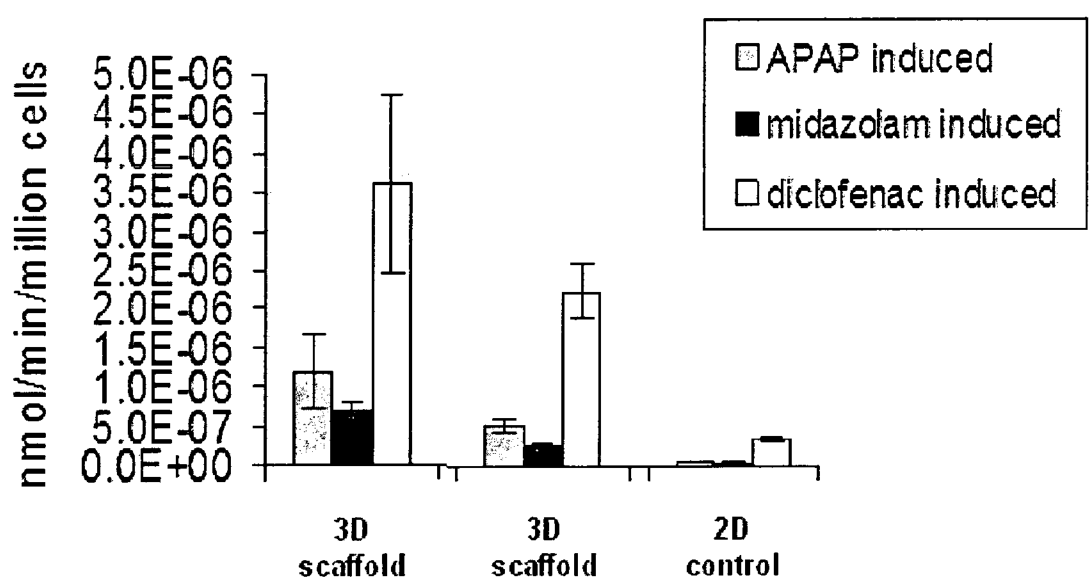
Figure 8:
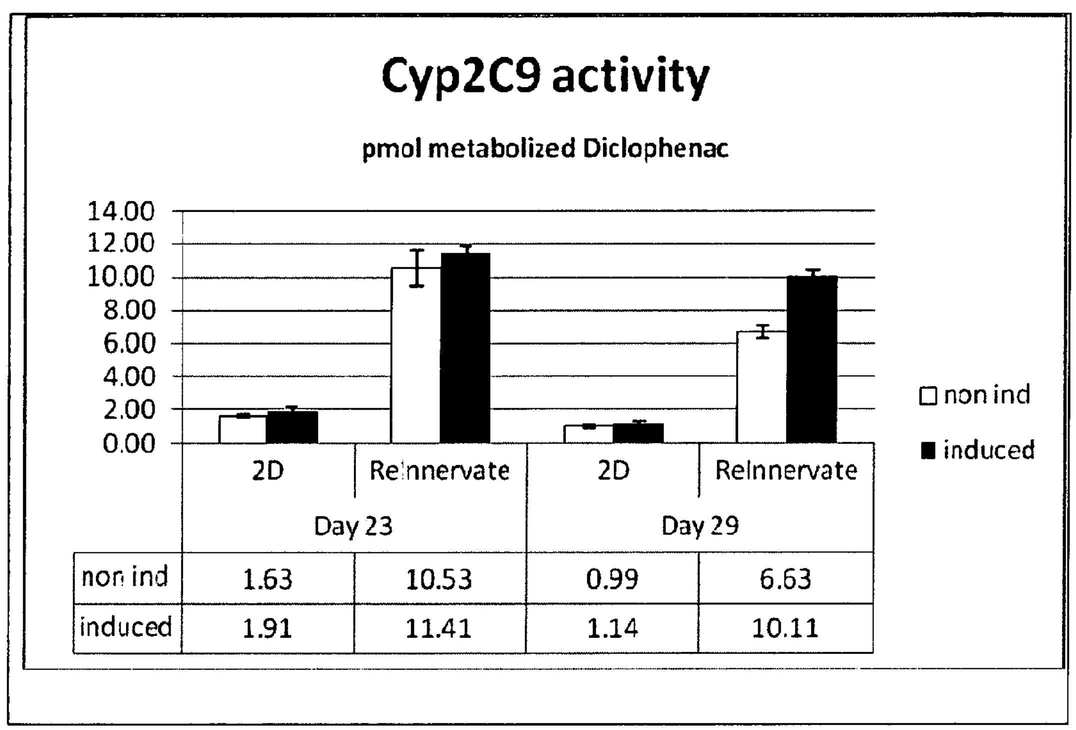
Figure 9:
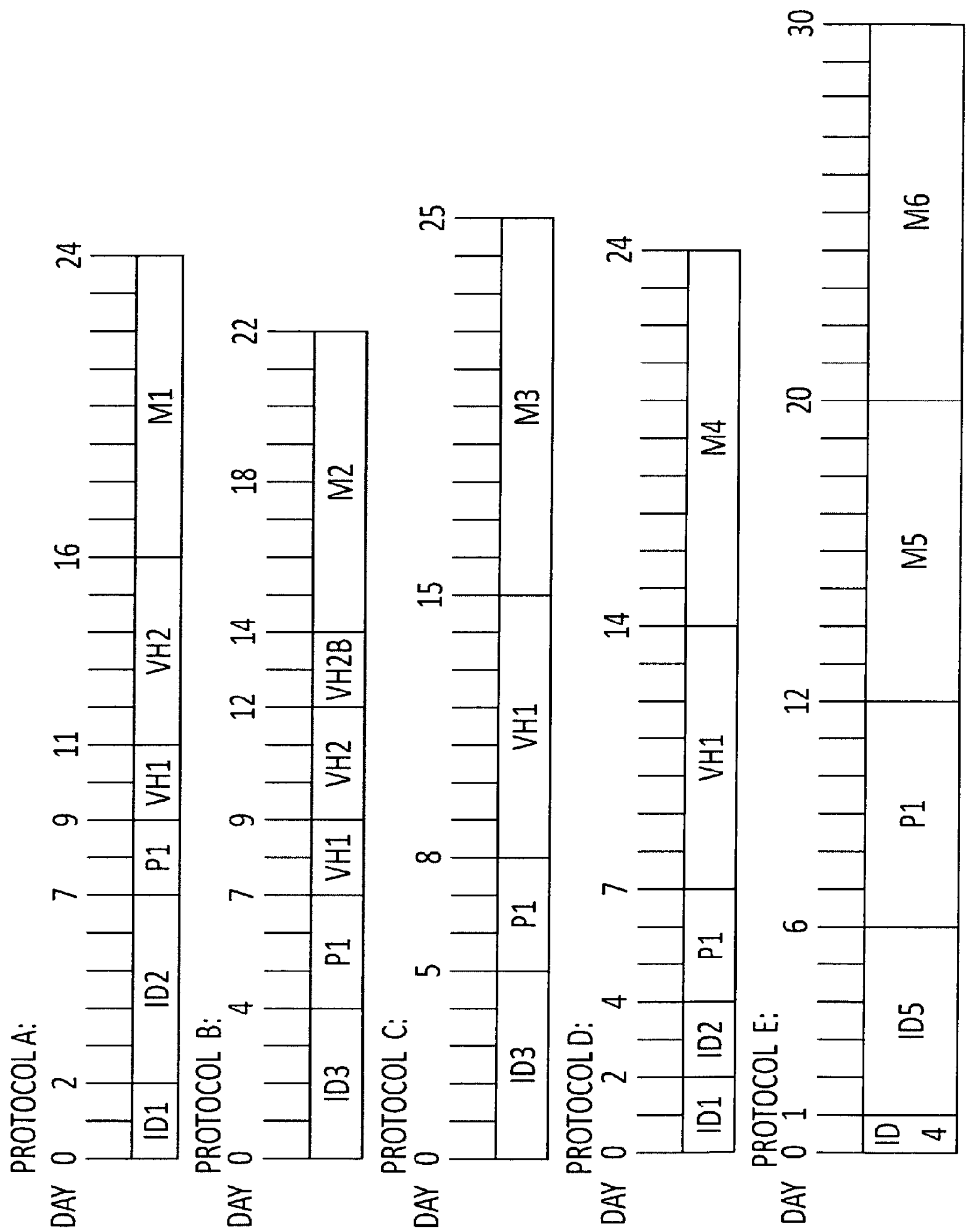
Figure 10:
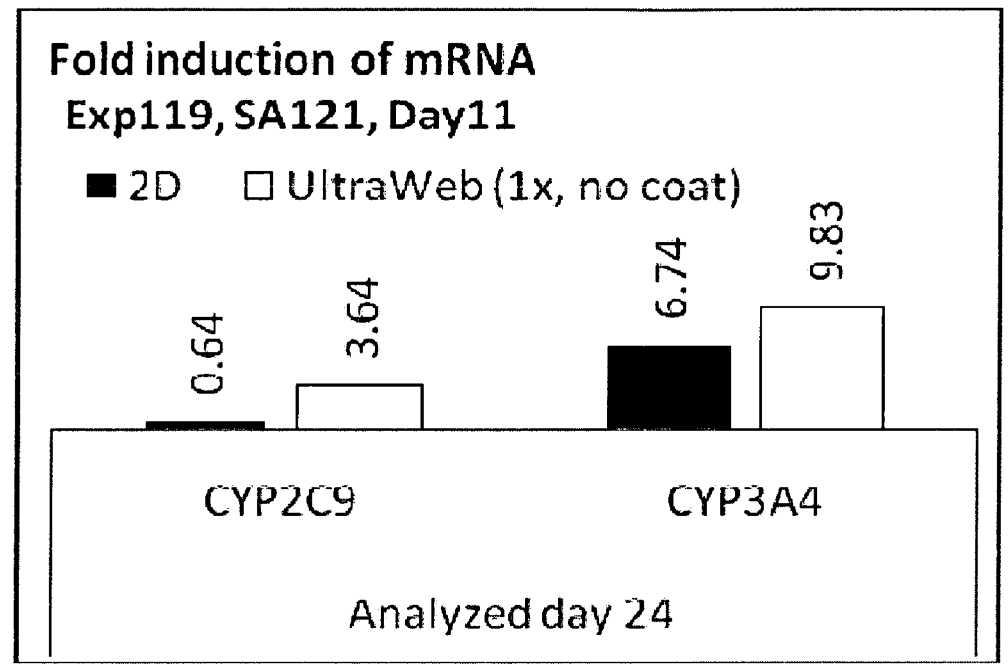
Figure 10:
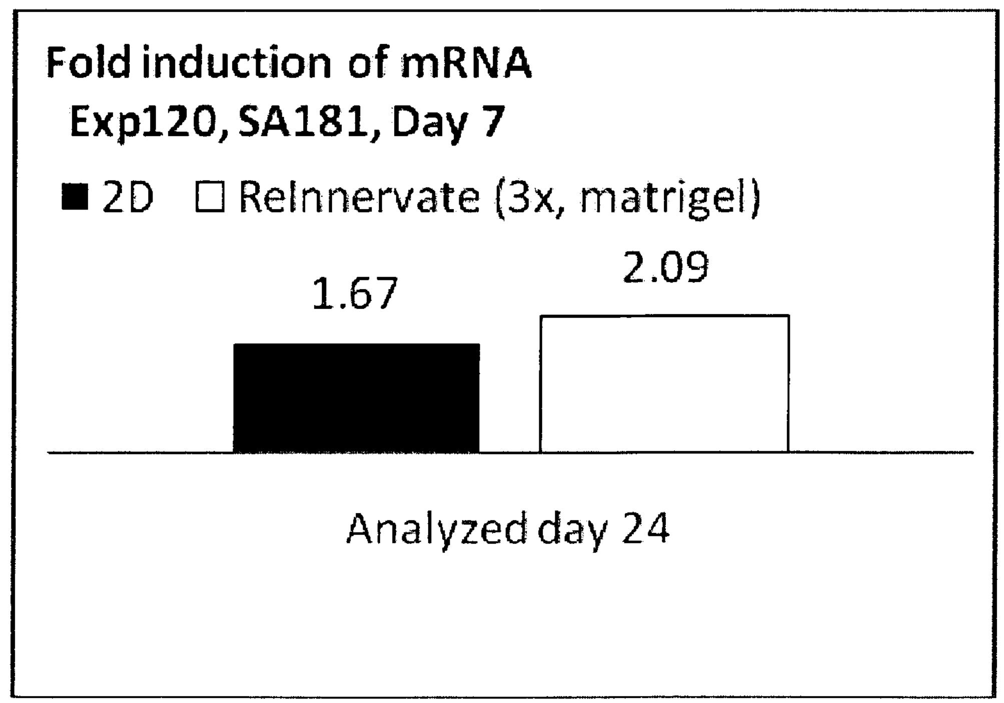
Figure 11A:
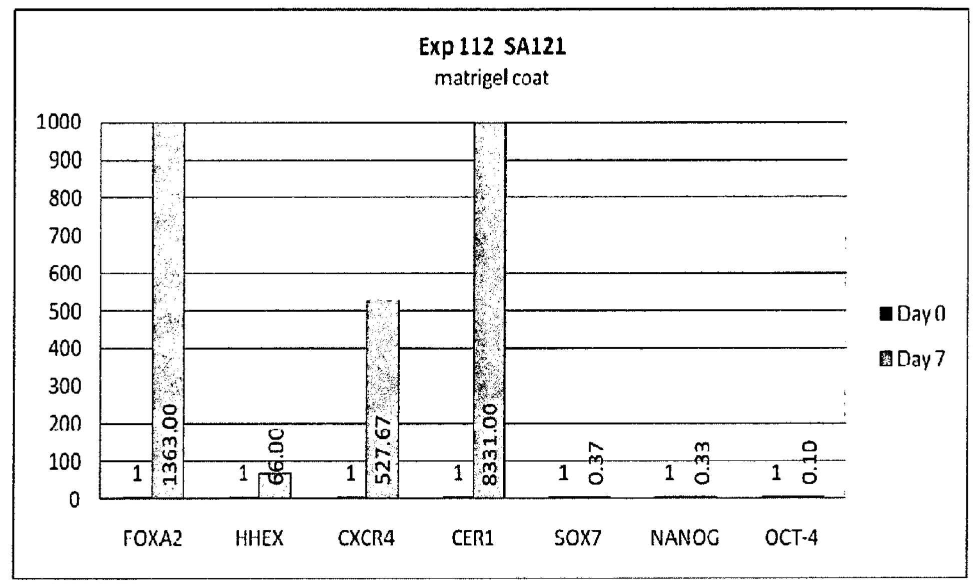
Figure 11A:
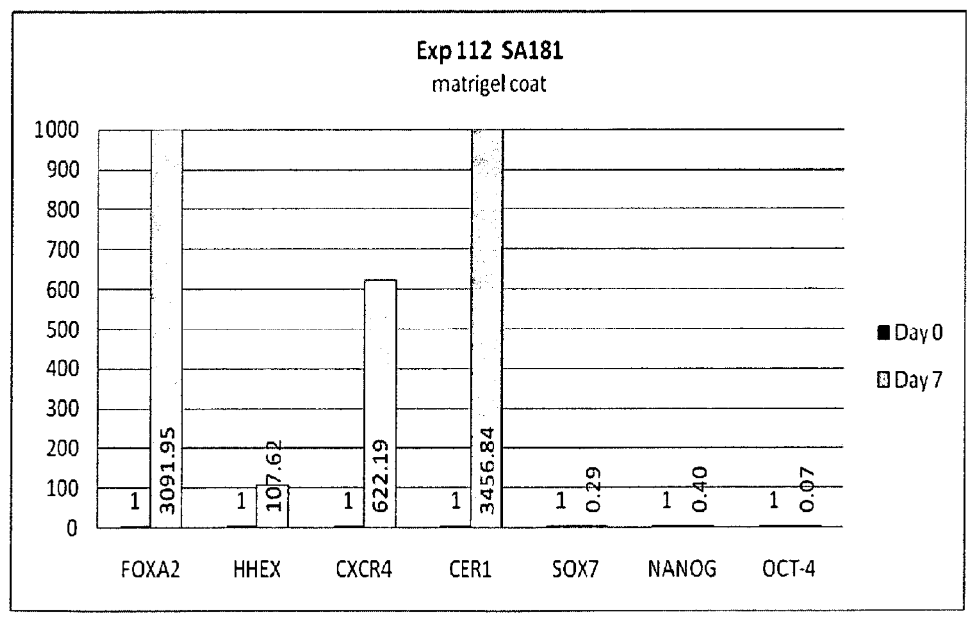
Figure 11B:
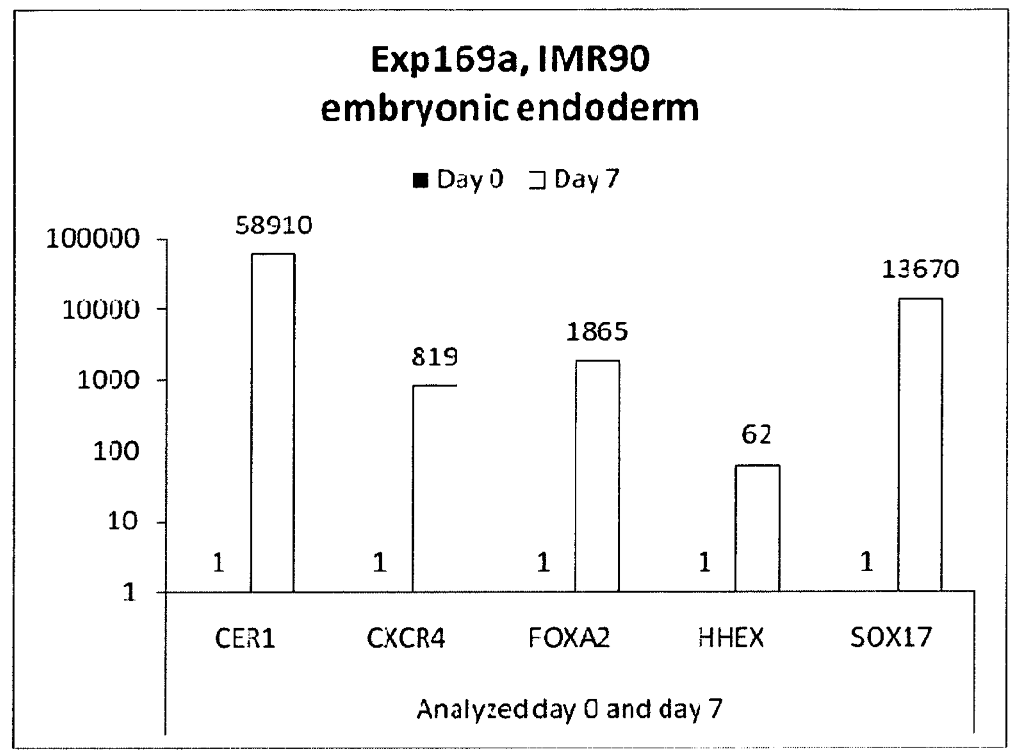
Figure 11B:
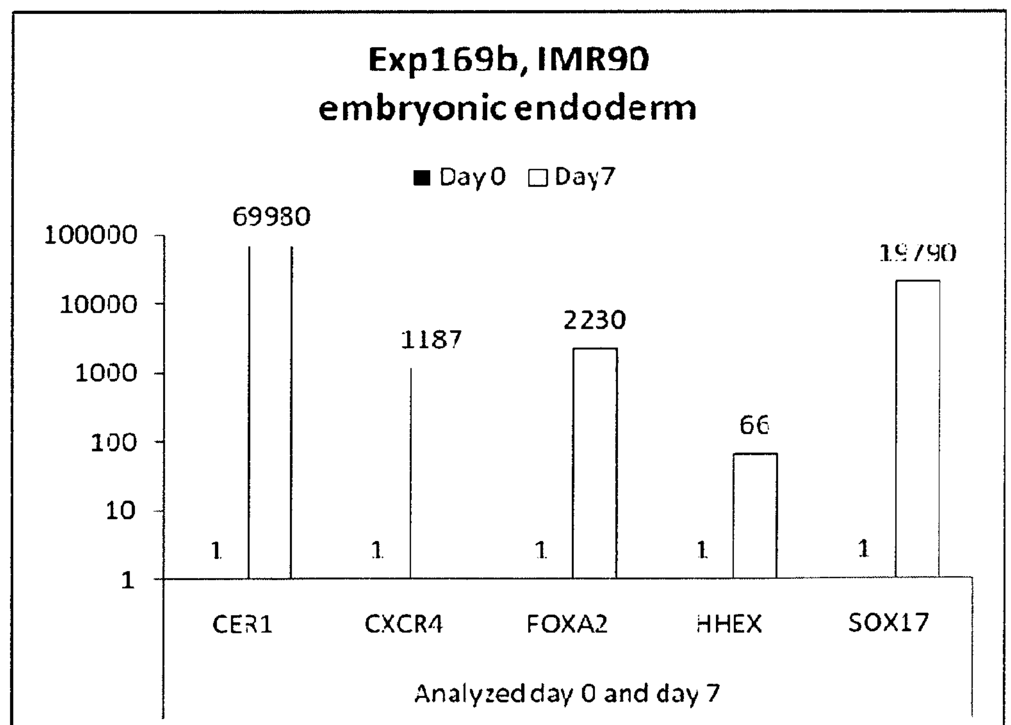
Figure 12:
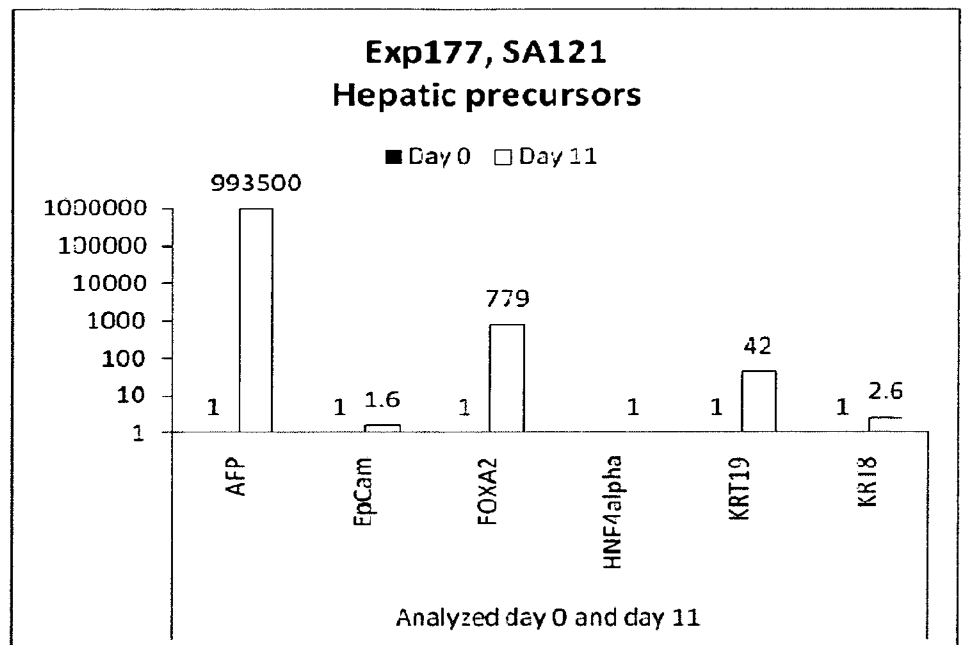
Figure 12:
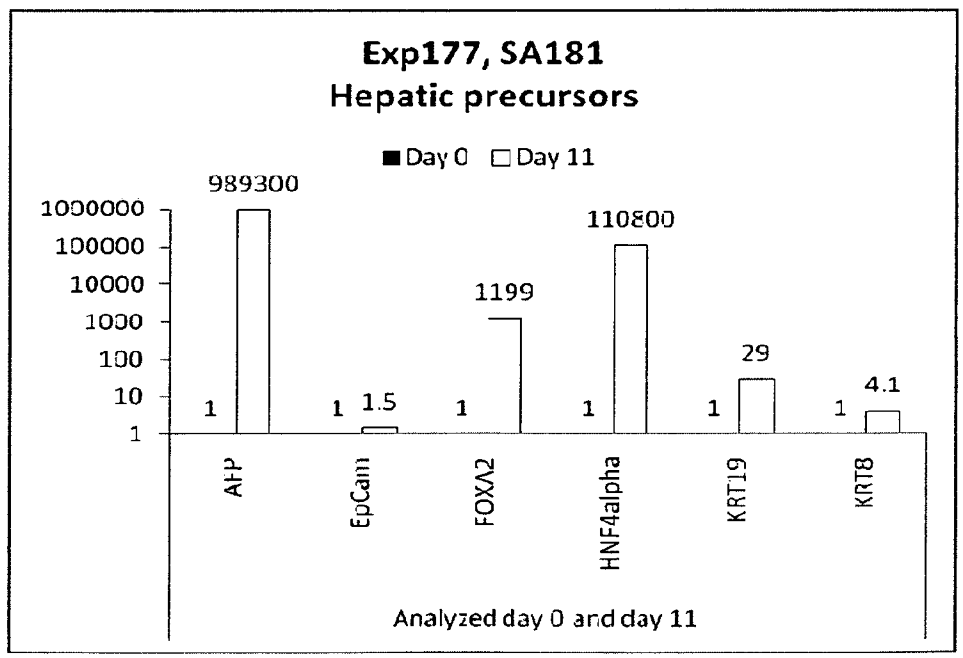

Relative expression levels of hepatic-markers on hESC-derived hepatocytes cultured either on 2D culture or 3D Artelon (Artimplant) scaffold. Artelon (Artimplant) is either uncoated or coated with matrix (Matrigel or gelatine) and cells seeded either at x1 density or ×3 density. Figure shows three independent cell lines (SA461, SA002, SA181) with cells cultured on scaffolds for either 0, 5, 11, 12, 14 or 15 days according to experiment numbers shown, protocols a) and c)

FIG. 2*a*.

hESC Derived Hepatocytes on AlgiMatrix.

Relative expression of hepatic markers on hESC-derived hepatocytes cultured either on 2D or 3D AlgiMatrix scaffold. Figures show two independent cell lines (SA002 and SA121) with cells cultured on scaffolds for either 14 or 13 days respectively, protocol d)

FIG. 2*b*.

iPS-Derived Hepatocytes on AlgiMatrix.

Relative expression of hepatic markers on iPS-derived hepatocytes cultured either in 2D or on 3D AlgiMatrix scaffold. Cells were differentiated for 7 days prior to seeding on scaffold and analysed after 32 days culture; protocol h (Exp169a) or f (Exp169b)

FIG. 3.

hESC Derived Hepatocytes on Ultra Web.

Relative expression of hepatic markers on hESC-derived hepatocytes cultured either on 2D or 3D Ultraweb scaffold. Ultraweb is either uncoated or coated with matrix (Matrigel or gelatine). Figures show four independent cell lines (SA002, SA461, SAl21 and SA181) with cells cultured on scaffolds for either 4, 5, 7 or 14 days, protocols a), b), c), d)

FIG. 4*a*.

hESC Derived Hepatocytes on Alvatex. (Reinnervate)

Relative expression levels of hepatic-markers on hESC-derived hepatocytes cultured either on 2D culture or 3D Alvatex (Reinnervate) scaffold. Alvatex is either uncoated or coated with matrix (Matrigel or gelatine) and cells seeded either at ×1 density or ×3 density. Figure shows four independent cell lines (SA461, SA002, SA181 and SA121) with cells cultured on scaffolds for either 0, 4, 9, 11, 13 or 14 days according to experiment numbers shown, protocols a), c), d)

FIG. 4*b*.

iPS Derived Hepatocytes on Alvatex. (Reinnervate)

Relative expression levels of hepatic-markers on iPS-derived hepatocytes cultured either on 2D culture or 3D Alvatex (Reinnervate) scaffold. Alvatex is either uncoated or coated with matrix (Matrigel or Fibronectin) and cells seeded after 7 days 2D culture at x6 density that of 2D cultures from which cells were harvested. Figure shows one independent iPS line (IMR90) with cells cultured on scaffolds for up to 29 days before analysis; culture protocol f.

FIG. 5*a* hESC-Derived Hepatocytes on Aggrewell

Relative expression levels of hepatic-markers on hESC-derived hepatocytes cultured either on 2D culture or 3D Aggrewell scaffold. Aggrewell is coated with matrix (Fibronectin) prior to seeding with cells cultured in 2D for 11 days; culturing according to protocol f) and cells seeded at either 100 or 200 aggregates per well. Figure shows one independent hESC line (SA181) with cells cultured on scaffolds for up to 25 days before analysis.

FIG. 5*b* iPS Derived Hepatocytes on Aggrewell

Relative expression levels of hepatic markers on iPS-derived hepatocytes cultured either on 2D culture or 3D Aggrewell scaffold. Aggrewell is coated with matrix (Fibronectin) prior to seeding with cells cultured in 2D for 7 days. Figure shows one independent iPS line (IMR90) with cells cultured on scaffolds for up to 29 days before analysis; culture protocol i)

FIG. 6

Relative expression of hepatic markers of hESC-derived hepatocytes cultured on Poly-l-lysine 3D scaffold (HAC). Cells were partially differentiated on 2D for 7 days prior to seeding and cultured until day 24 before analysis of marker expression; culture protocol g).

FIG. 7.

CYP Activities of hESC-Derived Hepatocytes in 3D Scaffolds. 3D Scaffold Left=Alvatex, 3D Scaffold Right=Ultra Web. Experiment 24, SA001 ECD.

Figure shows relative CYP activity of hESC-derived hepatocytes cultured either on Alvatex, Ultraweb or 2D control, with cells treated with either APAP, Midazolam or Diclofenac to induce CYP response and mimic hepatic metabolic activity.

FIG. 8.

CYP Induction in hESC Derived Hepatocytes Cultured in Either Conventional 2D Culture Plates or Alvatex Scaffolds.

Figures show CYP response in hESC-derived hepatocytes cultured either on Alvatex (Reinnervate) or 2D control, cells induced with Diclofenac to mimic hepatic liver activity. Activity assay performed at day 23 and day 29 as indicated.

FIG. 9.

Schematic of Differentiation Protocols Used to Differentiate hPS Cells to Hepatocytes.

Protocols a-e and respective experiment numbers together with duration of each experiment Protocol a: (exp 113, 114, 118, 119, 120).

2 Days ID1, 5 days ID2, 2 days P1, 2 days VH1, 5 days VH2, 8 days M1

Protocol b: (Exp104)

4 days ID3, 3 days P1, 2 days VH1, 3 days VH2, 2 days VH2B, 4 days or 8 days M2 (for cell cultures analyzed day 18 and day22 respectively)

Protocol c: (exp098)

5 days ID3, 3 days P1, 7 days VH1, 10 days M3

Protocol d: (exp088, 089)

2 days ID1, 2 days ID2, 3 days P1, 7 days VH1, 10 days of M4

Protocol e: (exp083)

1 day ID4, 5 days ID5, 6 days P1, 8 days M5, 15 days M6.

Protocol f: (exp169b, 172, 175SA181)

1 day ID1, 1 day ID6, 5 days ID2, 7 days VH1, then M1 till end of experiment

Protocol g: (exp139, 140, 148, 175SA121, 177SA121, CYP3A induction)

1 day ID7, 1 day ID8, 5 days ID9, 7 days VH1, then M1 till end of experiment

Protocol h: (exp169a, 177SA181, CYP3A induction)

1 day ID7, 1 day ID1, 5 days ID2, 7 days VH1, then M1 till end of experiment

Protocol i: (exp153)

1 day ID10, 1 day ID11, 2 days ID3, 7 days VH1, then M1 till end of experiment Detailed growth media composition used in protocols a to e

| Initial differentiation (ID) | | | |
|---|---|---|---|
| ID1 | ID2 | ID3 | ID4 |
| RPMI 1640 (+ 0.1% PEST, + 1% Glutamax)<br>1 × B27<br>100 ng/ml Activin A<br>1 mM NaB | RPMI 1640 (+ 0.1% PEST + 1% Glutamax)<br>1 × B27<br>100 ng/ml Activin A<br>0.5 mM NaB | RPMI 1640 (+ 0.1% PEST + 1% Glutamax)<br>1 × B27<br>100 ng/ml Activin A | Advanced RPMI 1640 (+ 0.1% PEST + 1% Glutamax)<br>100 ng/ml Activin A<br>0.5 ng/ml bFGF |
| ID5 | ID6 | ID7 | ID8 |
| Advanced RPMI 1640 (+ 0.1% PEST + 1% Glutamax)<br>100 ng/ml Activin A<br>0.5 ng/ml bFGF<br>0.2% FCS | RPMI 1640 (+ 0.1% PEST, + 1% Glutamax)<br>1 × B27<br>100 ng/ml Activin A<br>1 mM NaB<br>3 uM Chiron | mDEF<br>3 μM Chiron | RPMI 1640 (+ 0.1% PEST, + 1% Glutamax)<br>1 × B27<br>50 ng/ml Activin A<br>1 mM NaB |
| ID9 | | ID10 | |
| RPMI 1640 (+ 0.1% PEST + 1% Glutamax)<br>1 × B27<br>50 ng/ml Activin A<br>0.5 mM NaB | | RPMI 1640 (+ 0.1% PEST, + 1% Glutamax)<br>3 uM Chiron | |

| Hepatic Progenitor Media | | | |
|---|---|---|---|
| P1 | VH1 | VH2 | VH2B |
| RPMI A (+ 0.1% PEST, + 1% Glutamax)<br>100 ng/ml aFGF<br>5 ng/ml bFGF<br>50 ng/ml BMP2<br>200 ng/ml BMP4<br>0.2% FBS | VitroHES<br>1% DMSO | VitroHES<br>2% DMSO | VitroHES<br>2% DMSO<br>1.4 μM BIO |

| Maturation Media | | | |
|---|---|---|---|
| M1 | M2 | M3 | M4 |
| WME + SQ (−GA1000) (+1% Glutamax + 0.1% PEST)<br>10 ng/ml OsM<br>0.1 μM DexM<br>20 ng/ml HGF<br>0.5% DMSO<br>1.4 μM BIO | As M4 supplemented with 1.4 μM BIO | As M4 but using MEF conditioned WME + SQ (−GA1000) + 1% Glutamax + 0.1% PEST In stead of WME + SQ (− GA1000) + 1% Glutamax + 0.1% PEST). | WME + SQ (−GA1000) (+1% Glutamax + 0.1% PEST)<br>10 ng/ml OsM<br>0.1 μM DexM<br>2 ng/ml bFGF<br>10 ng/ml HGF<br>0.5% DMSO<br>10 mM Nicotinamide<br>ITS (1x, 10 μl/ml)<br>3 ng/ml glucagon |
| M5 | | M6 | |
| WME + SQ (−GA1000) (+1% Glutamax + 0.1% PEST)<br>2 ng/ml bFGF<br>20 ng/ml HGF | | WME + SQ (−GA1000) (+1% Glutamax + 0.1% PEST)<br>2 ng/ml bFGF<br>20 ng/ml HGF<br>10 ng/ml OsM<br>0.1 μM DexM | |

FIG. 10.

Induction of CYP Activities in 3D Scaffolds.

Induction of CYP3A and CYP2C9 activity by measuring the metabolic product of Midazolam, 4-OH Midazolam after 24 hours induction with or without 1 mM Phenobarbital and 10 uM Dexamethasone (induced/non-induced). During the 24 hours induction, Dexamethasone, DMSO and Bio was left out from the medium composition M1. After induction, the activity assay was performed as described elsewhere (see Example 6).

FIG. 11*a*.

Verification of Embryonic Endoderm Fate of hESC Cells Cultured on 2D Prior to Seeding on 3D Scaffolds.

Induction of endoderm markers (FoxA2, HHex, CxcR4, CER1) and downregulation of pluripotency markers (Sox7, Nanog, Oct4) in hESC cells cultured in 2D format for 7 days prior to seeding on 3D scaffolds; two independent cell lines (SA121 and SA181) cultured according to protocol a) on matrigel-coated 2D surface. Brightfield morphology of cells is also shown.

FIG. 11*b*.

Verification of Embryonic Endoderm Fate of iPS Cells Cultured on 2D Prior to Seeding on 3D Scaffolds.

Induction of endoderm markers (FoxA2, HHex, CxcR4, CER1) in iPS cells cultured in 2D format for 7 days prior to seeding on 3D scaffolds; cell line IMR90 cultured according to protocol h (exp169a) and f (exp169b)

FIG. 12.

Verification of Hepatic Progenitor Fate of hESC Cells Cultured on 2D Prior to Seeding on 3D Scaffolds.

Induction of hepatic progenitor markers (AFP, EpCAM, FOXA2, HNF4-a, KRT19, KRT8) in hESC cells cultured in 2D format for 11 days prior to seeding on 3D scaffolds; cell lines SA121 and SA181, cultured according to protocol g).

References

Baharvand, H. et al. (2006) Differentiation of human embryonic stem cells into hepatocytes in 2D and 3D culture systems in vitro. (2006) 50: 645-652

Berthiaume, F. et al. (1996) Effect of extracellular matrix topology on cell structure, function, and physiological responsiveness: hepatocytes cultured in a sandwich configuration. *FASEB J.* 10: 1471-1484

Blumenthal, B. et al. (2010) Polyurethane scaffolds seeded with genetically engineered skeletal myoblasts: a promising tool to regenerate myocardial function. *Artif. Organs* 34: E46-54 a. Bokhari, M. et al. (2007) Culture of HepG2 liver cells on three dimensional polystyrene scaffolds enhances cell structure and function during toxicological challenge. *J. Anat.* 211: 567-576 b. Bokhari, M. et al. (2007) Novel cell culture device enabling three-dimensional cell growth and improved cell function. *Biochem. Biophys. Res. Commun.* 354: 1095-1100

Dunn, J. C. et al. (1991) Long term in vitro function of adult hepatocytes in a collagen sandwich configuration. *Biotechnol. Prog.* 7: 237-245

Dvir-Ginzberg, M. et al. (2003) Liver tissue engineering within alginate scaffolds: effects of cell-seeding density on hepatocyte viability, morphology and function. *Tissue Eng.* 9: 757-766

Dvir-Ginzberg, M. et al. (2008) Induced differentiation and maturation of newborn liver cells into functional hepatic tissue in macroporous alginate scaffolds. *FASEB J.* 22: 1440-1449

Elkayam, T. et al. (2006) Enhancing the drug metabolism activities of C3A-a human hepatocyte cell line-by tissue engineering within alginate scaffolds. *Tissue Eng.* 12: 1357-1368

Hamilton, G. A. et al. (2001) Regulation of cell morphology and cytochrome P450 expression in human hepatocytes by extracellular matrix and cell-cell interactions. *Cell Tissue Res.* 306: 85-99

Heins, N. et al. (2004) Derivation, characterization, and differentiation of human embryonic stem cells. *Stem Cells* 22: 367-376

Matsumoto, K. et al. (2008) Hepatic differentiation of mouse embryonic stem cells in a three-dimensional culture system using polyurethane foam. *J. Biosci. Bioeng.* 105: 350-354

Piryaei, A. et al. (2010) Differentiation of Bone Marrow-derived mesenchymal stem cells into hepatocyte-like cells on nanofibers and their transplantation into a carbon tetrachloride-induced liver fibrosis model. *Stem Cell Rev. February* 25 (Epub ahead of print)

Rambhatla, L. et al. (2003) Generation of hepatocyte-like cells from human embryonic stem cells. *Cell Transplant* 12: 1-11

Shapiro, L & Cohen, S. (1997) Novel alginate sponges for cell culture and transplantation. *Biomaterials* 18: 583-90

Takahashi, K. et al. (2007) Induction of pluripotent stem cells from adult human fibroblasts by defined factors. *Cell* 131: 861-872

Thomson, J. A. et al. (1998) Embryonic stem cell lines derived from human blastocysts. *Science* 282: 1145-1147

Wang, S. et al. (2008) Three-dimensional primary hepatocyte culture in synthetic self-assembling peptide hydrogel. *Tissue Eng. Part A* 14: 227-236

Yu, J. et al. (2007) Induced pluripotent stem cell lines derived from human somatic cells. *Science* 318: 1917-1920.

The invention claimed is:

1. An in vitro method for differentiating human pluripotent stem (hPS) cells into hepatocyte-like cells or mature hepatocytes comprising:

i) Seeding and differentiating hPS cells into definitive endoderm (DE) cells on a 2-dimensional surface; and ii) Transferring the DE cells of step i) after 4 to 7 days to a 3-dimensional (3D) scaffold and further differentiating the DE cells seeded onto the 3D scaffold into hepatocyte-like cells or mature hepatocytes.

2. A method according to claim 1, wherein the cells are seeded at higher density on the 3D scaffolds than on the 2D cultures.

3. The method according to claim 1 wherein the cells are seeded in the presence of cell survival factor.

4. A method according to claim 1, wherein at least one of the steps i) or ii) is performed under feeder-free conditions.

5. A method according to claim 1, wherein at least one of the steps i) or ii) is performed under xeno-free conditions.

6. A method according to claim 1, wherein the hPS cells are xeno-free cells.

7. A method according to claim 1, wherein the hPS cells are human embryonic stem (hES) cells.

8. A method according to claim 1, wherein the hPS cells are induced pluripotent stem (iPS) cells.

9. A method according to claim 1, wherein the 3D scaffold is chosen from one of the following:

i) a porous alginate sponge;

ii) a biodegradable poly(urethaneurea) (PUUR) polymer;

iii) an emulsion-templated polystyrene;

iv) a synthetic nanofibrillar composite; and v) a porous sponge fabricated from Poly (L-lactic Acid).

10. A method according to claim 9, wherein the 3D scaffold is a porous alginate sponge which has a pore size of 50-200 μm.

11. A method according to claim 9, wherein the 3D-scaffold is an emulsion templated polystyrene scaffold which has a pore size in the range of 0.1-1000 μm.

12. A method according to claim 1, wherein the 3D-scaffold is uncoated.

13. A method according to claim 1, wherein the 3D-scaffold is pre-coated with one or more extracellular matrix components.

14. A method according to claim 13, wherein the one or more extracellular matrix components is selected from a list comprising: gelatine, laminin, fibronectin, collagen, polylysine, vitronectin, hyaluronic acid, hyaluronan hydrogels, silk fibroin, chitosan or a composite of any of the forementioned.

15. A method according to claim 1, wherein the scaffold is contained within a suitable culture vessel.

16. A method according to claim 1, wherein the hepatocyte cells display elevated metabolic activity as shown by increased expression of one or more CYP markers.

17. A method according to claim 1, wherein the hepatocyte cells display increased expression of one or more hepatic-associated transporter proteins.

18. A method according to claim 1, wherein the proportion of hepatocytes compared to non-hepatocyte cells is greater than 5%.

19. A method according to claim 1, wherein the DE cells are co-cultured on the 3D scaffolds with at least one other cell type chosen from, but not limited to: stellate hepatic cells, hepatic immune (Kuppfer) cells, hepatic endothelial cells, biliary epithelial cells or fibroblasts.

20. A method according to claim 2, wherein the cells are seeded on the 3D scaffold at a density which is threefold higher or fivefold higher or tenfold higher than on the 2D cultures.

21. A method according to claim 3, wherein the cell survival factor is an inhibitor of ROCK Rho kinase.

22. A method according to claim 11, wherein the pore size is in the range of 15-45 μm.

23. A method according to claim 15, wherein the culture vessel is a multiwell plate.

24. A method according to claim 23, wherein the multiwell plate is selected from the group consisting of a 6-well plate, a 12-well plate, a 24-well plate, a 48-well plate, a 96-well plate, a 384-well plate, and a 1536-well plate.

25. A method according to claim 1, wherein the proportion of hepatocytes compared to non-hepatocyte cells is greater than 10%.

26. A method according to claim 1, wherein the hepatocyte cells display increased expression of one or more hepatic-associated transporter proteins selected from BSEP, FABP1, MRP2, NTCP, OATP2 and OCT1.

* * * * *